(12) United States Patent
Eastin et al.

(10) Patent No.: US 12,172,174 B1
(45) Date of Patent: Dec. 24, 2024

(54) SYSTEMS FOR THE CONTROL AND USE OF FLUIDS AND PARTICLES IN ELECTROSPINNING, MATS, WOUND DRESSINGS, SEED COATINGS, AND POWDERS, AND IN FORMATION OF NANOPARTICLES, NANO-FIBERS, NANO-STRUCTURES, NANOPARTICLE SUSPENSIONS, MICRO-PARTICLES, MICRO-FIBERS, MICRO-STRUCTURES, AND MICRO-PARTICLE SUSPENSIONS

(71) Applicant: Kamterter Products, LLC, Waverly, NE (US)

(72) Inventors: John Alvin Eastin, Waverly, NE (US); David Vu, Waverly, NE (US)

(73) Assignee: Kamterter Products, LLC, Waverly, NE (US)

(*) Notice: Subject to any disclaimer, the term of this patent is extended or adjusted under 35 U.S.C. 154(b) by 1416 days.

(21) Appl. No.: 16/184,800

(22) Filed: Nov. 8, 2018

Related U.S. Application Data

(60) Provisional application No. 62/583,374, filed on Nov. 8, 2017.

(51) Int. Cl.
| | |
|---|---|
| B05B 12/08 | (2006.01) |
| B01J 2/06 | (2006.01) |
| B05D 1/02 | (2006.01) |
| B82Y 5/00 | (2011.01) |
| B82Y 40/00 | (2011.01) |
| D01D 5/00 | (2006.01) |
| D01D 4/02 | (2006.01) |

(52) U.S. Cl.
CPC ............ B05B 12/08 (2013.01); D01D 5/0038 (2013.01); B01J 2/06 (2013.01); B05D 1/02 (2013.01); B82Y 5/00 (2013.01); B82Y 40/00 (2013.01); D01D 4/02 (2013.01); D01D 5/0069 (2013.01)

(58) Field of Classification Search
CPC .................... B05B 12/08; B05B 12/10; B01J 2219/00243
See application file for complete search history.

(56) References Cited

U.S. PATENT DOCUMENTS

| | | | | |
|---|---|---|---|---|
| 9,148,994 B1* | 10/2015 | Eastin | ................ | A01M 7/0092 239/8 |
| 2005/0091021 A1* | 4/2005 | Gupta | .................... | C08F 10/02 703/12 |
| 2008/0228321 A1* | 9/2008 | van Wijck | .............. | C01B 3/025 700/268 |
| 2009/0241817 A1* | 10/2009 | Eastin | ................ | A01M 7/0092 239/8 |
| 2018/0117609 A1* | 5/2018 | Hodgkinson | ............. | B05B 7/22 |
| 2018/0153206 A1* | 6/2018 | Eastin | .................... | A23P 10/40 |

* cited by examiner

Primary Examiner — John J DeRusso
(74) Attorney, Agent, or Firm — Suiter Swantz IP

(57) ABSTRACT

Nanotechnology applications including nanomedicine, nano-suspensions including colloids, nanopillars, tissue engineering, drug delivery, semiconductor fabrication, nanotube fabrication, nanowire fabrication, nano-fuels incorporate low pressure or low energy processes to emit, extrude, deliver, or distribute viscous fluids. Fixtures, applicators, application configurations, and operational parameters and dimensions may be determined, limited, and selected based on a lability characteristic of a feedstock ingredient with respect to a lability reference frame.

10 Claims, 15 Drawing Sheets

Prior art

Prior Art

Prior Art

SYSTEMS FOR THE CONTROL AND USE OF FLUIDS AND PARTICLES IN ELECTROSPINNING, MATS, WOUND DRESSINGS, SEED COATINGS, AND POWDERS, AND IN FORMATION OF NANOPARTICLES, NANO-FIBERS, NANO-STRUCTURES, NANOPARTICLE SUSPENSIONS, MICRO-PARTICLES, MICRO-FIBERS, MICRO-STRUCTURES, AND MICRO-PARTICLE SUSPENSIONS

PRIORITY

The present application is related to and claims the benefit of the earliest available effective filing date(s) from the following listed application(s) (the "Related Applications") (e.g., claims earliest available priority dates for other than provisional patent applications or claims benefits under 35 USC § 119 (e) for provisional patent applications, for any and all parent, grandparent, great-grandparent, etc. applications of the Related Application(s)).

RELATED APPLICATIONS

For purposes of the USPTO extra-statutory requirements, the present application constitutes a nonprovisional application of provisional patent application Ser. No. 62/583,374 entitled SYSTEMS FOR THE CONTROL AND USE OF FLUIDS AND PARTICLES IN ELECTROSPINNING, MATS, WOUND DRESSINGS, SEED COATINGS, AND POWDERS, AND IN FORMATION OF NANOPARTICLES, NANO-FIBERS, NANO-STRUCTURES, NANOPARTICLE SUSPENSIONS, MICRO-PARTICLES, MICRO-FIBERS, MICRO-STRUCTURES, AND MICRO-PARTICLE SUSPENSIONS, naming John Alvin Eastin and David Vu as inventor, filed Nov. 8, 2017. U.S. Provisional patent application Ser. No. 62/583,374 is incorporated by reference in its entirety.

TECHNICAL FIELD

The present invention generally relates to nanotechnology, and, in particular, electrospinning, mats, wound dressings, seed coatings, powders, and formation of suspensions.

BACKGROUND

Nanoparticles are classified by their size, ranging from 1 to 100 nanometers (nm) in size. Nanotechnology is the manipulation of nanoparticles.

Industries involving nanomedicine, nano-suspensions including colloids, nanopillars, tissue engineering, drug delivery, semiconductor fabrication, nanotube fabrication, nanowire fabrication, nano-fuels, and other nanoscale applications are experimenting with nanotechnology. Products are being developed using nanotechnology that provide improvements at both micro and macro levels. By creating a product at the molecular level, the external and interactive properties of that product are more readily and predictably directed to a desired result.

Delivery and distribution mechanisms used in nanotechnology often deliver or distribute particles using high energy or high pressure. These high-energy or high-pressure applications are not cost- or energy-effective.

Therefore, improved apparatuses and methods for nano-related applications are needed.

SUMMARY

Apparatuses and methods for nanoparticle delivery and distribution are disclosed. In one aspect, a method for labile-based spray and emission for nanotechnology applications is disclosed. The method may include an act of determining a lability reference frame for a feedstock. The method may include an act of comparing first lability characteristics of the feedstock at a first point in the lability reference frame with second lability characteristics of the feedstock at a second point in the lability reference frame to determine a level of lability of the feedstock. The method may include an act of limiting a spectrum of selection criteria or configuration criteria based on the level of lability. The method may include an act of converging on a value to determine an adjustment, a calibration, a dimensional, or an operational parameter using the limit and at least one of the first lability characteristics and the second lability characteristics.

Apparatuses and methods for nanotechnology applications in which delivery means and/or distribution means are tailored to the specific nanotechnology application are disclosed. Dimensions of the distribution means including spray fixtures are adjusted based on feedstock characteristics, propellant characteristics, or combinations thereof. Dimensions of the delivery means including pressure, flow rates, tube/pipe diameters, friction coefficients, temperature (e.g., pre-heat temperature), and combinations thereof are adjusted based on feedstock characteristics, propellant characteristics, or combinations thereof.

In another aspect, the inventive concepts are directed to a method of distribution or delivery of nanoparticles for nanotechnology applications based on lability characteristics. The method may include an act of selecting one or more emission, extrusion, or distribution applications from among multiple nanotechnology applications. The method may include determining one or more spray, emission, extrusion, or distribution, forms and associated spray, emission, extrusion, or distribution parameters. The method may include an act of determining feedstock characteristics including at least one of lability, thermodynamic, fluidic, and kinematic properties and associating the feedstock characteristics with a lability reference frame. The method may include an act of providing fixture selection or configuration criteria based on 1) the lability reference frame, 2) the feedstock characteristics, 3) the spray, emission, extrusion, or distribution, forms, and 4) the lability reference frame.

In another aspect, the inventive concepts are directed to a system for delivery and distribution of nanoparticles for nanotechnology applications based on lability characteristics. The system may include an applicator having an adjustable speed and comprising a first port, a second port, and at least one adjustable valve, each of the first port and the second port being configured for interchangeably receiving one or more components based on lability characteristics of a feedstock. The system may include a selected feedstock hopper having a third port configured to interface with the first port. The system may include a selected distribution mechanism having a fourth port configured to interface with the second port, the distribution mechanism being coupled with the feedstock hopper via one or more delivery mechanisms and configured to spray or emit the feedstock at least proportionally to the adjustable speed and according to the lability characteristics of the feedstock, the spray or emission being adjustable using the adjustable valve.

BRIEF DESCRIPTION OF THE DRAWINGS

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings.

Figure 14:
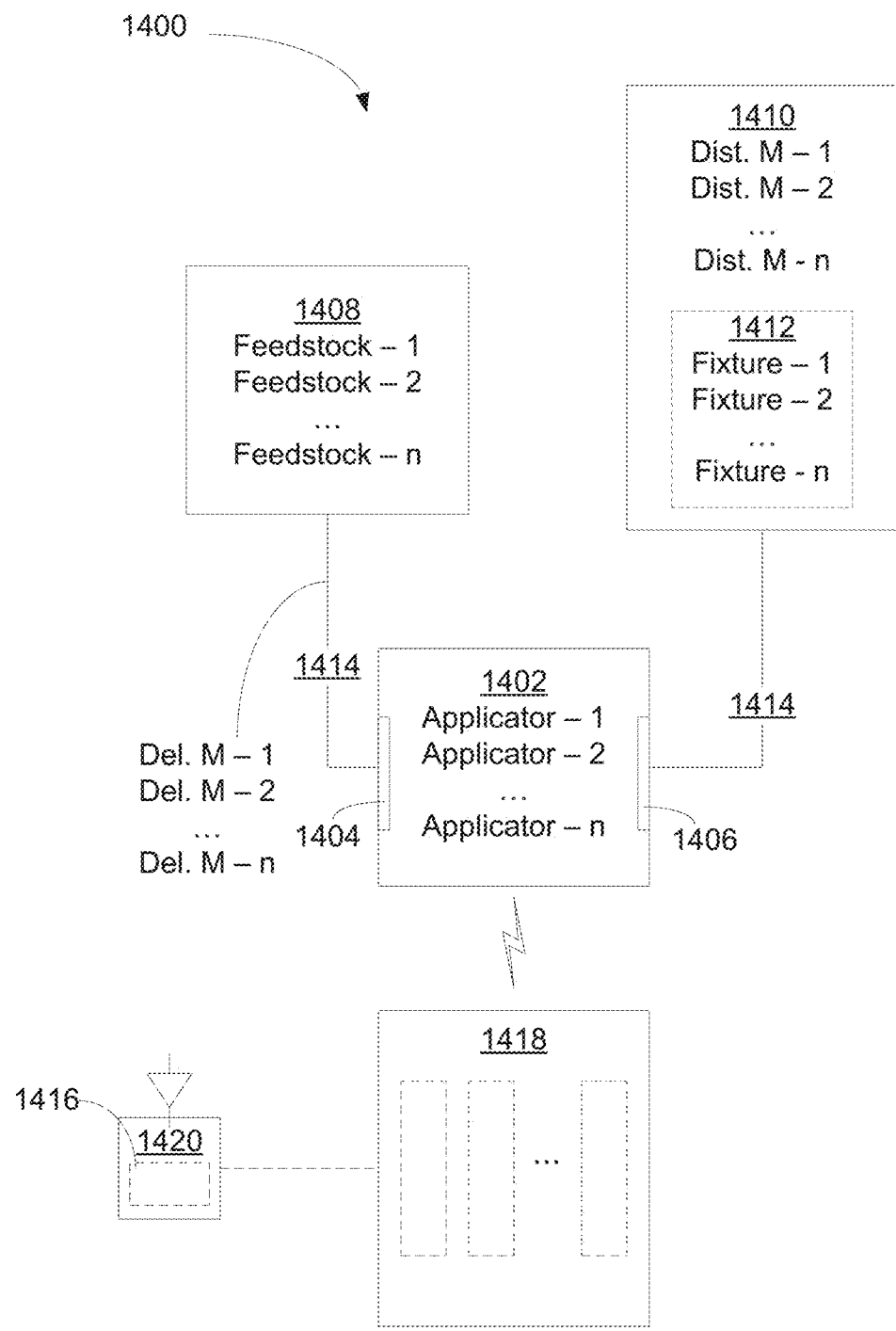
Figure 15:
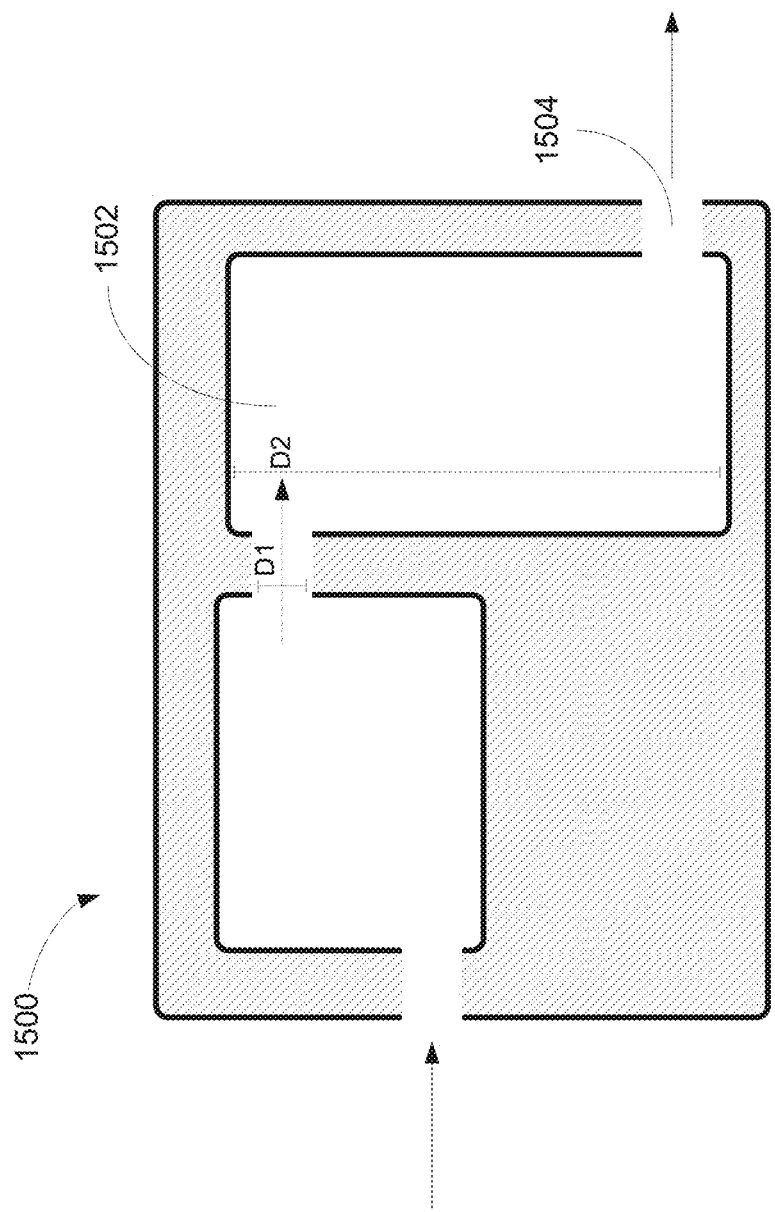
Figure 16:
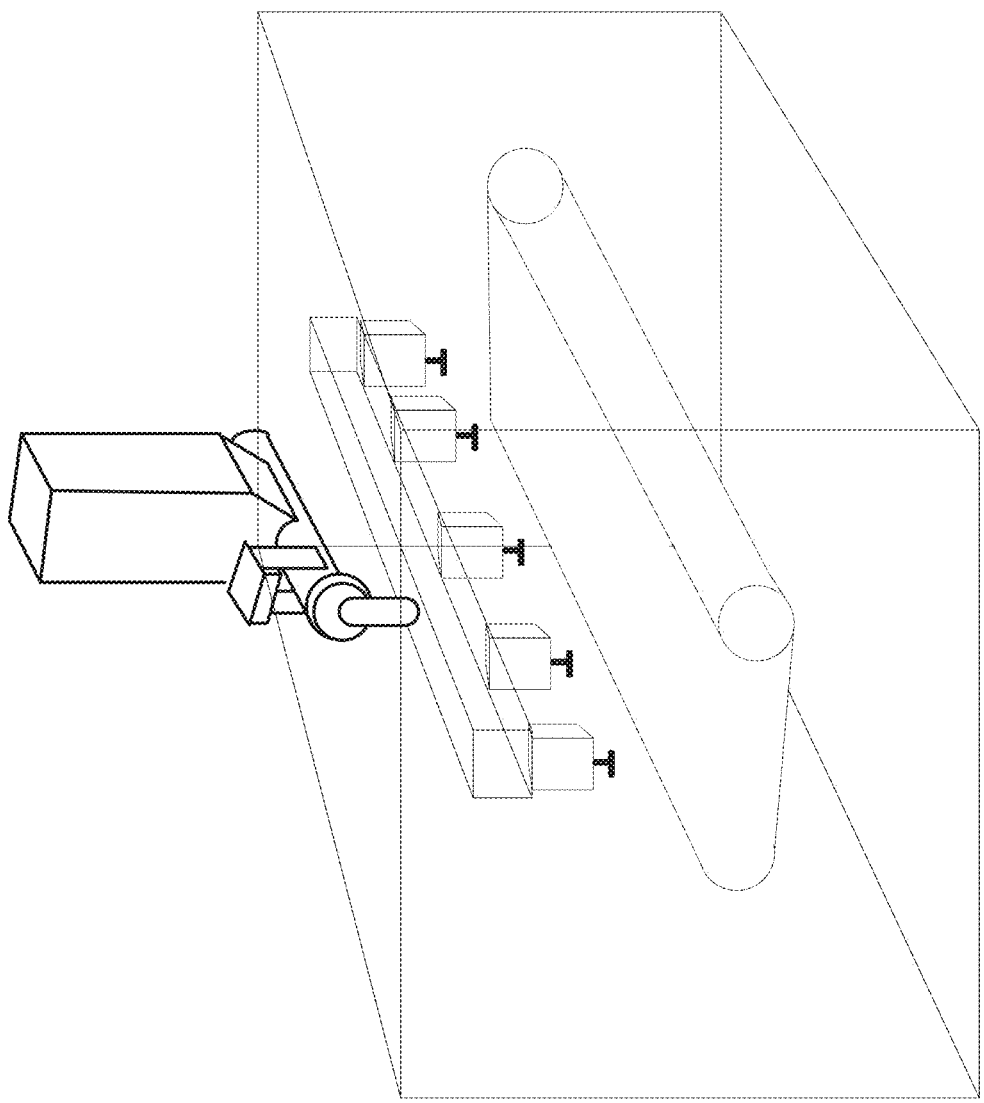

FIG. 14 is an embodiment of a system for delivery and distribution for nanotechnology applications based on lability characteristics, according to the inventive concepts disclosed herein; and FIG. 15 is an embodiment of a fluid dampener, according to the inventive concepts disclosed herein; and FIG. 16 is an embodiment of an applicator and applicator configuration, according to the inventive concepts disclosed herein.

DETAILED DISCLOSURE

"Delivery mechanism" as used herein includes, but is not limited to, an auger within a delivery tube, multiple augers within a delivery chamber or a large delivery tube, a low pressure pump (e.g., peristaltic, gear, etc.), inlets and/or outlets, a fluid line, a valve, a hopper sized or angled for effective delivery, an electric charge, a needle-like column, adjustable opposing plates, a spray fixture, capillary forces, and combinations thereof.

"Distribution mechanism" as used herein includes, but is not limited to, a spray fixture, a nozzle, spray outlets, delivery tube outlets, a shearing knife, an opening between a plate of a fixture, and combinations thereof.

"Propellant" as used herein includes a low to medium viscosity fluid used to propel an oil, ingredient, fluid, particle, semi-solid, slurry, emulsion, colloidal suspension, or a combination thereof, out of a distribution mechanism. The propellant generally combines its kinetic energy with the kinetic energy of the material being propelled (e.g., utilizes mostly constructive forces as opposed to destructive forces). The propellant generally has a lower viscosity than the material it propels. However, in embodiments in which propelled ingredients are vaporized and/or atomized prior to being delivered, the propellant may have a higher or similar viscosity as compared to the material being propelled. The propellant is often air, but may include other low to medium viscosity fluids such as inert gases, carbon dioxide, or combinations thereof.

"Feedstock material" any oils, ingredients, fluids, particles, semi-solids, slurries, emulsions, colloidal suspensions, or combinations thereof, delivered via a delivery mechanism disclosed herein to a distribution mechanism. The feedstock material generally has a high viscosity, such as a non-Newtonian fluid. The feedstock generally has a higher viscosity than the propellant. However, it is noted that in some applications, feedstock ingredients may be vaporized prior to mixing, and in such cases, the feedstock may have a lower or similar viscosity as compared to the propellant.

"Distributing" as used herein shall mean any form of moving, collecting, spraying or otherwise disposing of groups, patterns, or individual distributed forms of at least one of the following: fluid flow, drop, slurry, globule, fiber, particle, vapor, and mist.

"Spray fixture" or "nozzle" as used herein shall mean an apparatus adapted to be connected to a source of feedstock material or fuel and to a force for powering or propelling the feedstock material or fuel through the apparatus, the apparatus including an outlet and structure for controlling the output of feedstock material from the outlet of the spray fixture. The spray fixture encompasses more structure than a nozzle, and therefore in embodiments a spray fixture encompasses a nozzle, but not visa-verse.

"Newtonian fluid" a fluid that obeys Newton's law of viscosity, represented as follows:

$$\tau = \mu \frac{dV}{dy}$$

or in other words, where the shear stress, $\tau$ ($N/m^2$), is linearly proportional to the velocity gradient $dV/dy$, and where $\mu$ is dynamic viscosity ($N \cdot s/m^2$), $dV$ is unit velocity (m/s), and $dy$ is unit distance between layers (m).

"Non-Newtonian fluid" as used herein shall mean fluids that contain suspended particles or dissolved molecules. This term may include, but is not limited to, Bingham fluids, pseudoplastic fluids, dilatant fluids, thixotropic fluids, and viscoelastic fluids. The term shall include, but is not limited to, fluids whose characteristics are represented by the Ostwald-de Waele equation as follows:

$$\tau = K\left(\frac{dV}{dy}\right)^n$$

where K (often in kg/ms$^{2-n}$) and n (dimensionless) are constants determined by experimental fitting data. Generally, for pseudoplastic fluids, n is less than 1 and for dilatant fluids n is greater than 1.

"Labile" as used herein shall mean ingredients, components, particles, and/or fluids that are susceptible to changing state or losing a characteristic after prolonged contact with another ingredient, component, particle, and/or fluid. For example, an aromatic hydrocarbon is a labile ingredient that loses a liquid characteristic when subjected to air or fairly low temperatures.

"Viscosity" as used herein shall mean dynamic viscosity measured at room temperature (e.g., 20° C.) unless specifically specified otherwise.

"High viscosity" or "highly viscous fluids" as used herein includes fluids having a viscosity within the range of 0.8 to 10 kg/m·s (800 to 10,000 cP), inclusive. In some embodiments, the high viscosity fluids may be higher than 10 kg/m·s Examples of fluids having high viscosity include dispersions, suspensions, or emulsions (e.g., oil emulsions). For instance, glycerol having an apparent viscosity of 1.412 kg/m·s (1412 cP) may be considered a high viscosity fluid. Corresponding yield stress, τ, will vary depending on the fluid, but generally ranges from 10-200 Pa.

"Medium viscosity" with respect to fluids, includes a fluid having a viscosity within the range of $0.86 \times 10^{-3}$ to 0.08 kg/m·s (0.86 to 80 cP), inclusive. Examples of fluids having medium viscosity include Menhaden fish oil (used in some liquid fertilizers). In some embodiments, a medium viscosity fluid is from 1 cP, inclusive, to 800 cP, exclusive.

"Low viscosity" with respect to fluids, includes a fluid having a viscosity within the range of $0.97 \times 10^{-5}$ to $2.28 \times 10^{-5}$ kg/m·s (0.0097 to 0.0228 cP). Examples of fluids having low viscosity include air, nitrogen, and Xenon. In some embodiments, a low viscosity fluid is from 0.0097 cP, inclusive, to 1 cP, exclusive.

"Emulsifying agent" or "emulsifier" as used herein includes a substance that has hydrophobic and hydrophilic properties, allowing dissolution of the substance in fatty or oily solutions and in aqueous solutions. The term shall encompass fertilizer related emulsifying agents, including but not limited to, polyoxyethylene esters of fatty acids, polyoxyethylene glycol esters of fatty acids, polyoxyethylene sorbitan esters of fatty acids, propylene glycol esters of fatty acids, alkyl aryl polyether alcohols, organic phosphate esters, salts of alkyl aryl sulfonates, salts of fatty alcohol sulfates, alkyl aryl polyether sulfonates, sarcosinate salts, protein condensates, fatty acid amines, fatty amine condensates, amine salts of sulfonic acids, esters of sodium sulfosuccinic acid, and combinations thereof.

"Encapsulation" as used herein includes a method/process for distributing (e.g., entrapping) a first fluid component (e.g., particulate, pollutant, etc.) within a second fluid component (e.g., high viscosity fluid, carrier, amphiphilic component, or combinations thereof). In embodiments, this delivery of the first component within a second component may delay emission of a volatile pollutant, partially isolate the first component, encircle a portion of the feedstock material including the first component within a coating or a shell, affect a reaction rate of the first component, and combinations thereof. For instance, a result of encapsulation may include improving a delayed release characteristic, delaying delivery and/or emission until the first component reaches an action or reaction site (e.g., roots of a certain type of plant), improving a preservation characteristic (e.g., by providing a barrier between the first component and one or more reactants), generating particles with a size of a few nanometers or millimeters, and combinations thereof.

"Amphiphile" as used herein means a molecule with both hydrophilic and hydrophobic properties.

"Wetting agent" as used herein means a fluid used to wet or change a density of particulates in process air or intended for process air. The term may also be used with respect to a compound, molecule, and/or fluid that affects a surface tension of a substance.

"Low Pressure" as used herein means pressure sufficiently low that the need of high powered compressors and high pressure delivery means are negated. For example, low pressures may be from 1-15 psi or 6.89 to 103.42 kPa, inclusive.

Low pressure delivery methods and apparatuses are disclosed herein.

In some embodiments, a shear plate or shear force, is used to separate and deliver portions of feedstock material to delivery tubes, fixtures, and/or application surfaces (e.g., orifice, filters, filter media, etc.).

In some embodiments, fixtures have two or more separate fluid flow paths and only combine the fluid flow paths just before delivery. In other embodiments, fixtures allow fluid flow paths to combine prior to and during delivery, effecting improved mixing and resulting a sprayed emulsion. Fluid flow paths of fixtures are adjustable to affect fluid dynamics and distribution patterns.

In some embodiments, fixtures are configured for ligament extrusion. These fixtures generally have two or more fluid paths and ligament extrusion and stretching occurs as a fluid from each path is brought into contact with each other.

In some embodiments, fixtures can variably adjust fluid delivery, which accordingly adjusts associated Reynolds numbers.

In some embodiments, labile ingredients are mixed with precision to avoid degradation and/or emission. In other embodiments, immiscible liquids are mixed with precision for improved uniformity in extrusion concentration or fiber/particle application.

In some embodiments, high viscosity fluids are mixed with, or have suspended therein, solid particles to deliver suspensions and/or emulsions for a nanotechnology application. In these embodiments, the feedstock physical and energy characteristics often resemble those of non-Newtonian fluids.

The apparatuses, methods, principles, and inventive concepts disclosed herein, are related to nanotechnology applications, and shall be applicable to nanoparticle industries, colloids, nanopillars, tissue engineering, drug delivery, semiconductor fabrication, nanotube fabrication, nanowire fabrication, nano-fuels, other nanoscale applications, and combinations thereof.

Methods and apparatuses related to fixtures, nozzles, delivery mechanisms, distribution mechanisms, mixing, ligament formation and extrusion, and/or distributing immiscible ingredients, and combinations thereof, are described generally in U.S. Pat. No. 9,148,994, issued on Oct. 6, 2015, filed Nov. 12, 2012, by John Alvin Eastin, et al., which is incorporated herein by reference in its entirety.

In many of nanotechnology applications, ingredients do not mix well together. In many of these techniques and/or applications, reaction times of ingredients must be limited to decrease undesired chemical reactivity (e.g., degradation). In many of these techniques and/or applications, ingredients should not be mixed by delivery mechanisms prior to a desired point (e.g., extraction, extrusion, and stretching point). In many of these techniques and/or applications effective delivery may be proportional to, or affected by, particle size (e.g., as with colloidal suspensions). In many of these techniques and/or applications a batch or a continuous process is required for an effective nanoparticle application (e.g., formation of medicinal mats). In most of these techniques and/or applications, it is desirable to reduce production costs associated with conventional feedstock delivery. In many of these techniques and/or applications, delivery mechanisms should not result excessive clogging at inlets or outlets or require excessive pulsation and vibrations to minimize the clogging. Further, these delivery mechanisms should be easily adjustable to deliver variable, desirable fiber dimensions, forms, particles, or nanoparticle patterns.

Figure 1:
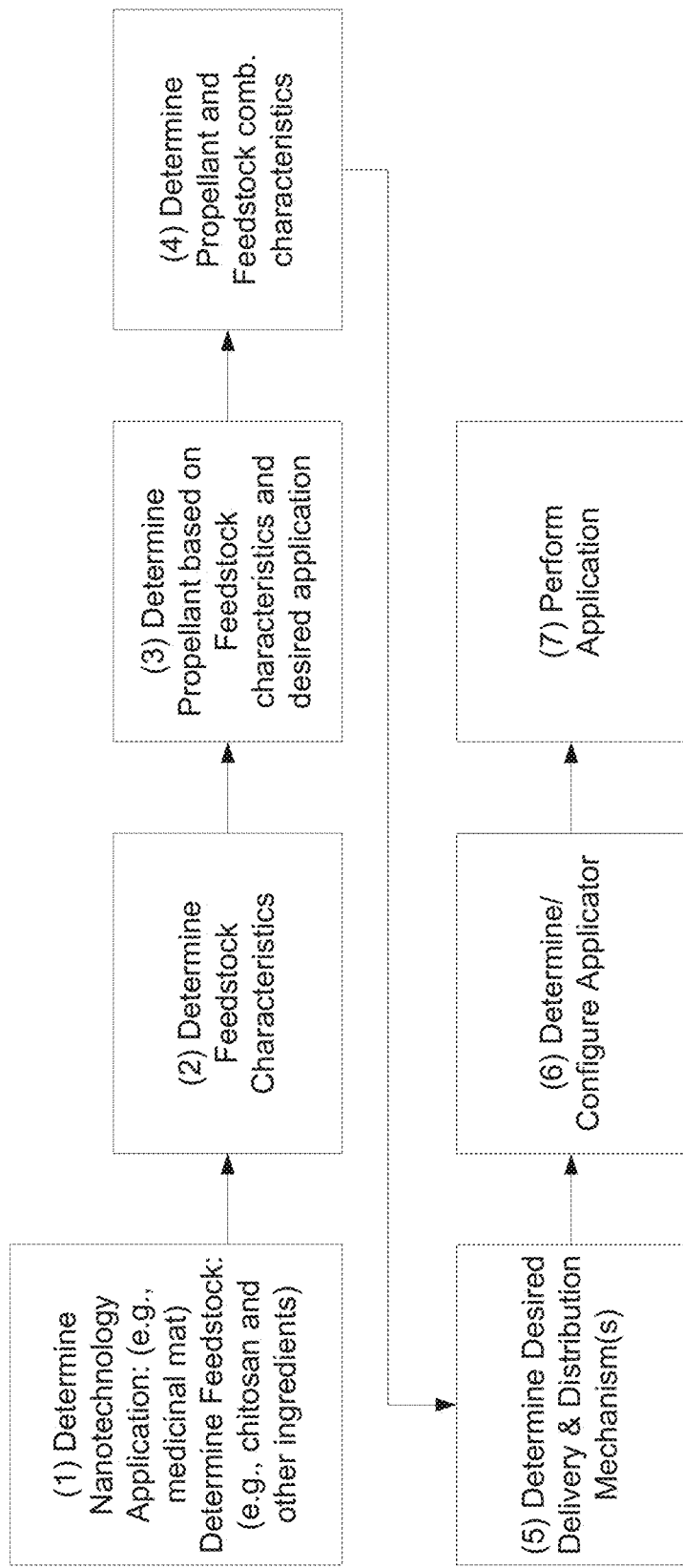
FIG. 1 is an embodiment of a flow diagram of a method for limiting selection or configuration criteria, according to the inventive concepts disclosed herein.
Figure 2:
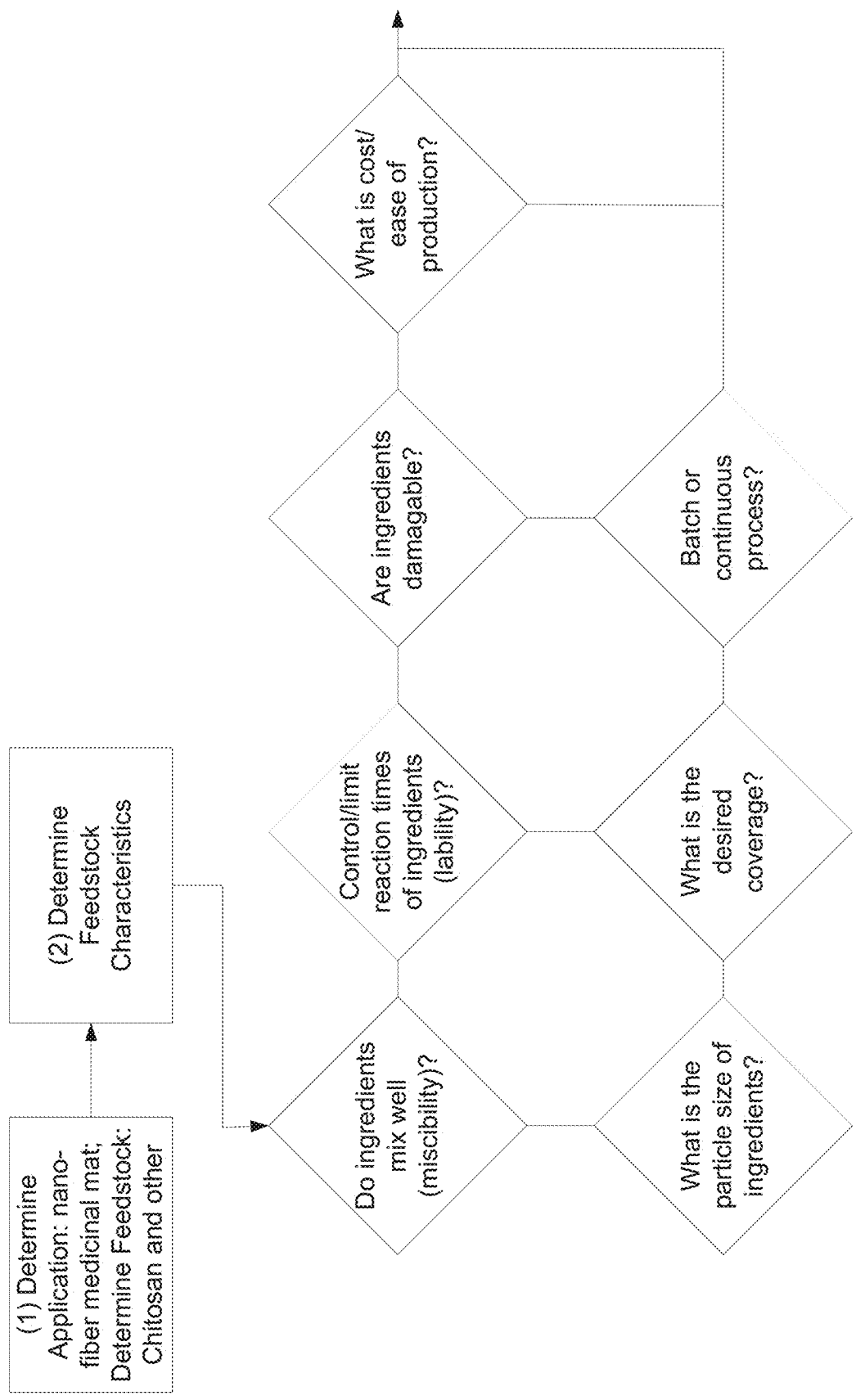
FIG. 2 is an embodiment of a flow diagram of a method for limiting selection or configuration criteria, according to the inventive concepts disclosed herein.
Figure 3:
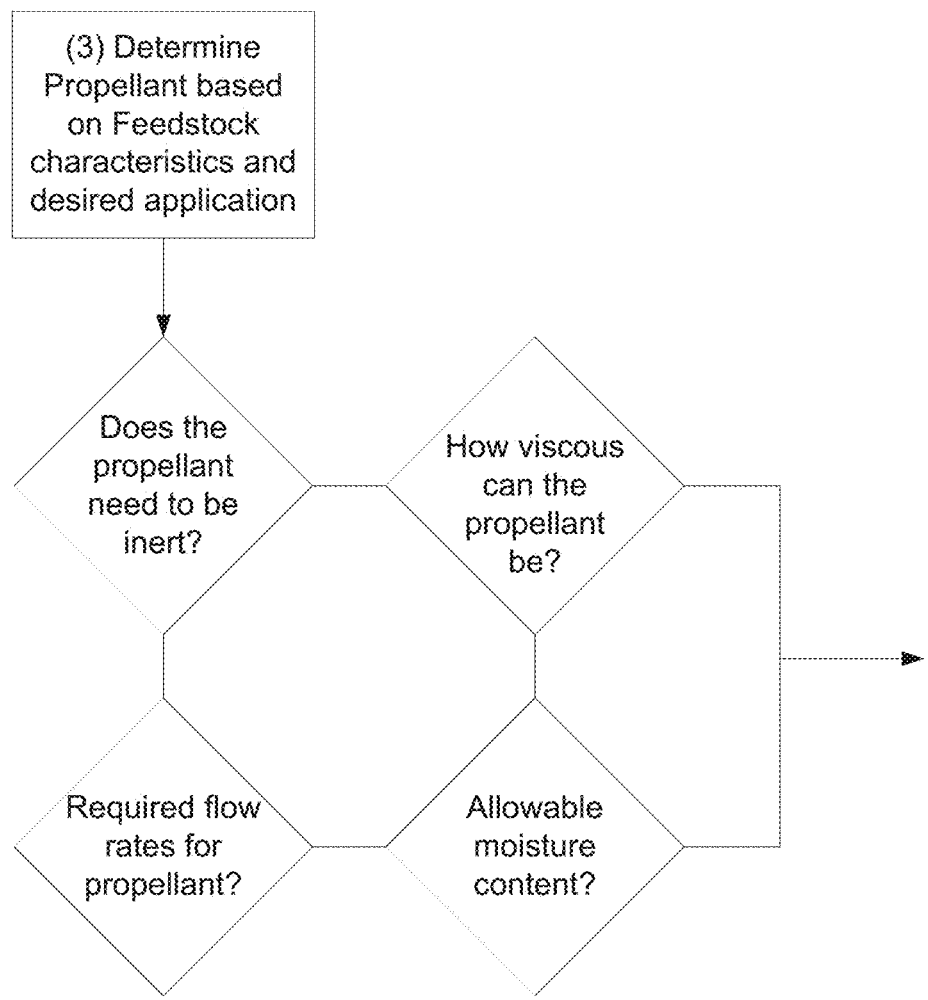
FIG. 3 is an embodiment of a flow diagram of a method for limiting selection or configuration criteria, according to the inventive concepts disclosed herein.
Figure 4:
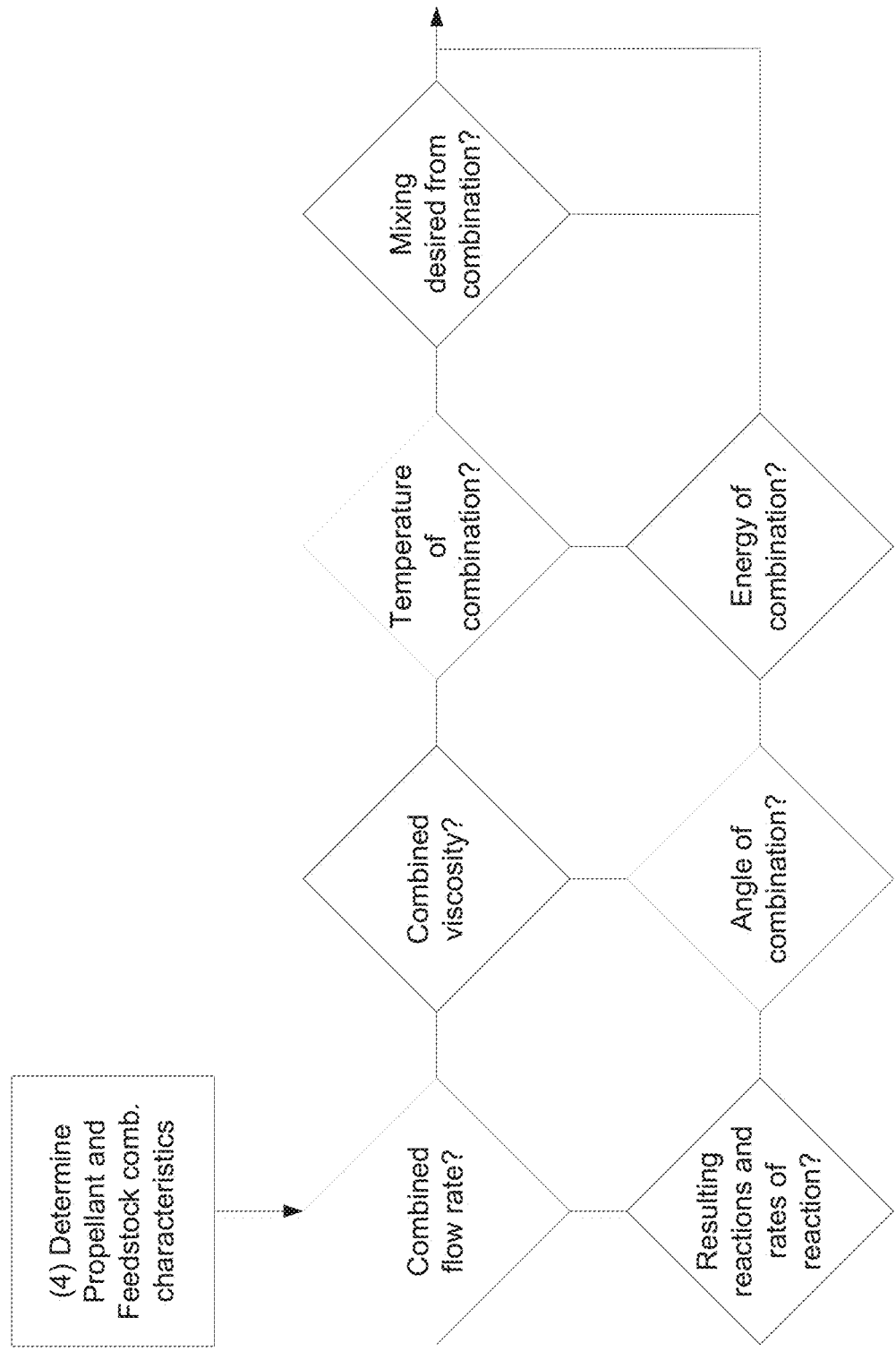
FIG. 4 is an embodiment of a flow diagram of a method for limiting selection or configuration criteria, according to the inventive concepts disclosed herein.
Figure 5:
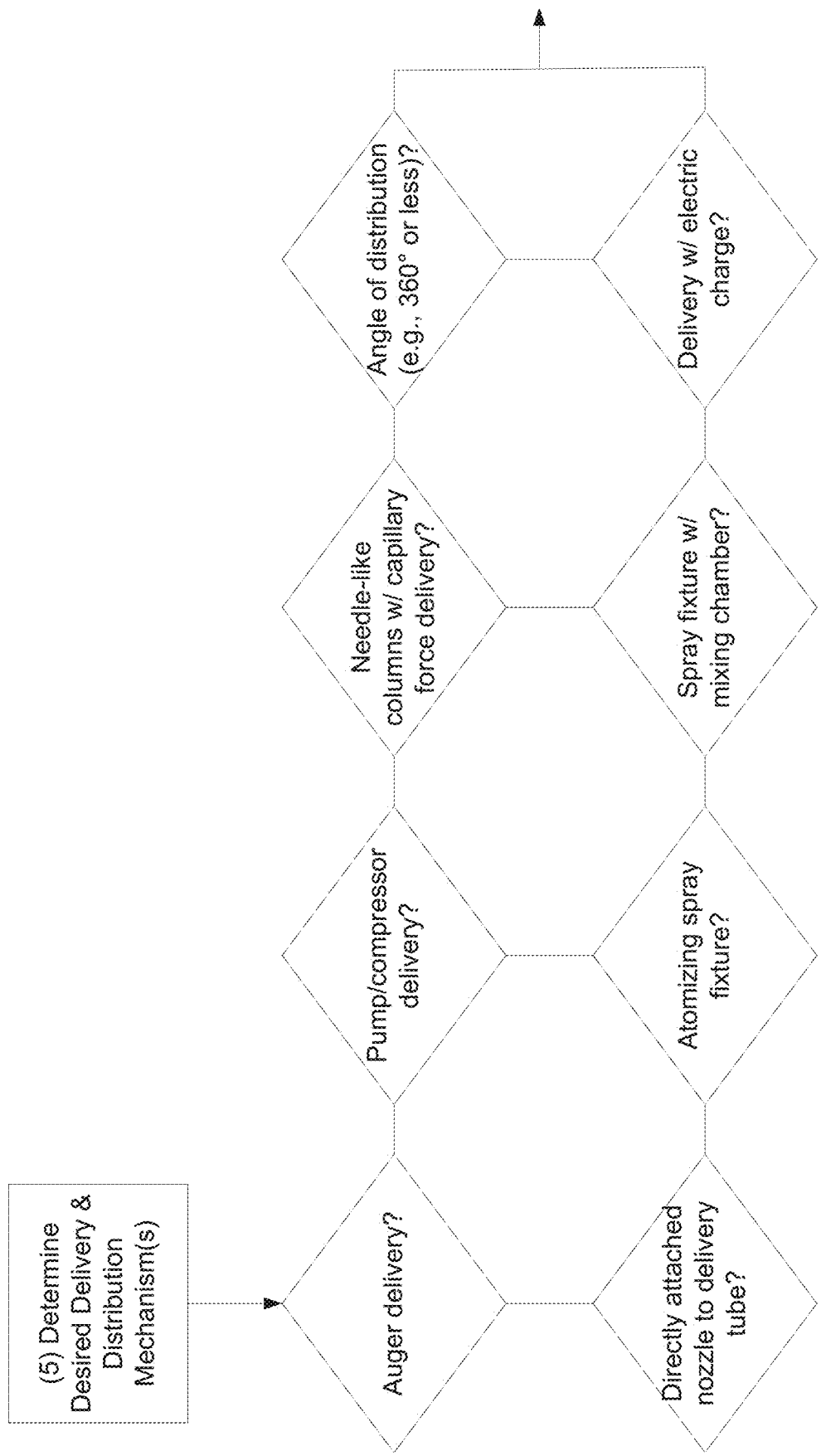
FIG. 5 is an embodiment of a flow diagram of a method for limiting selection or configuration criteria, according to the inventive concepts disclosed herein.
Figure 6:
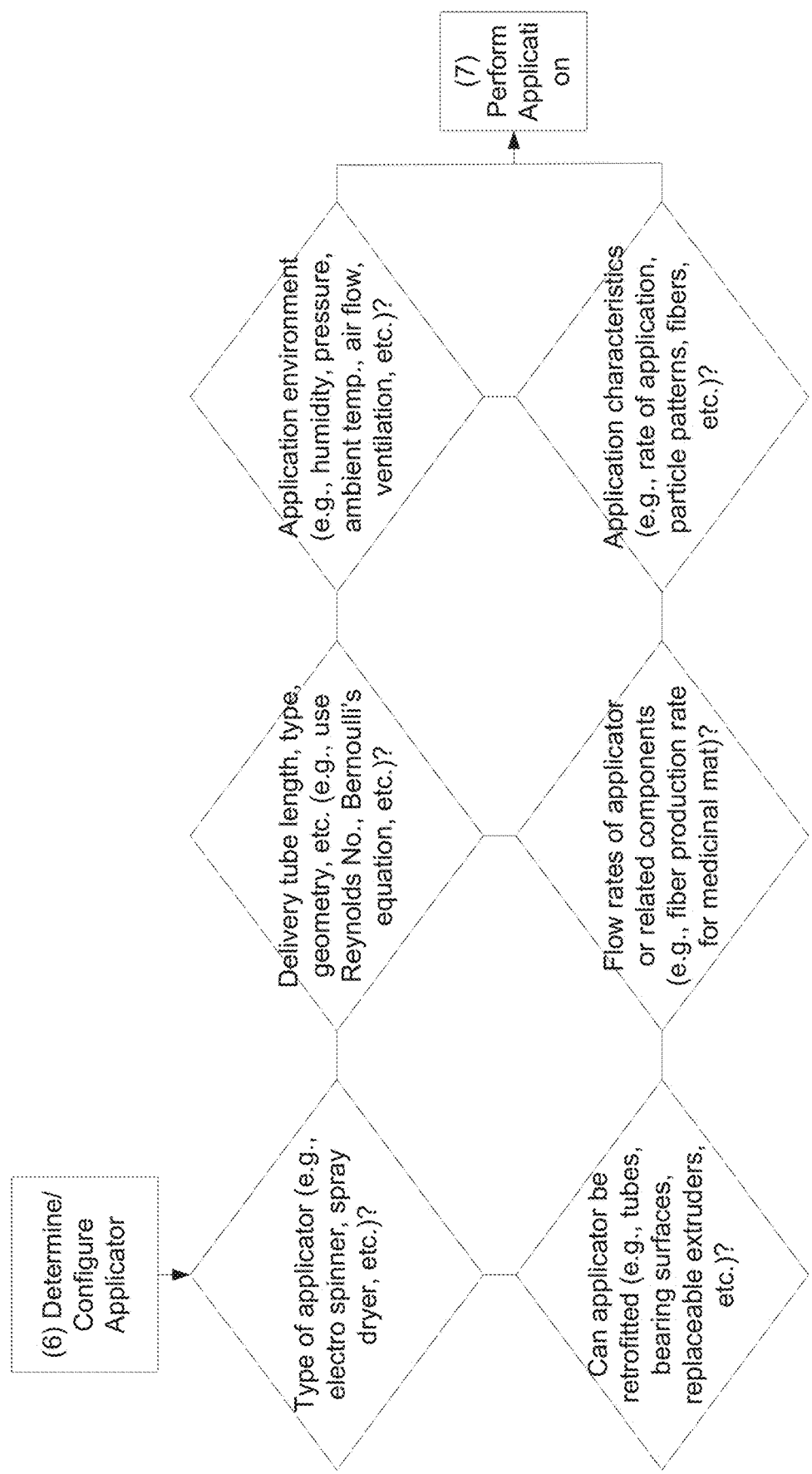
FIG. 6 is an embodiment of a flow diagram of a method for limiting selection or configuration criteria, according to the inventive concepts disclosed herein.
Figure 7:
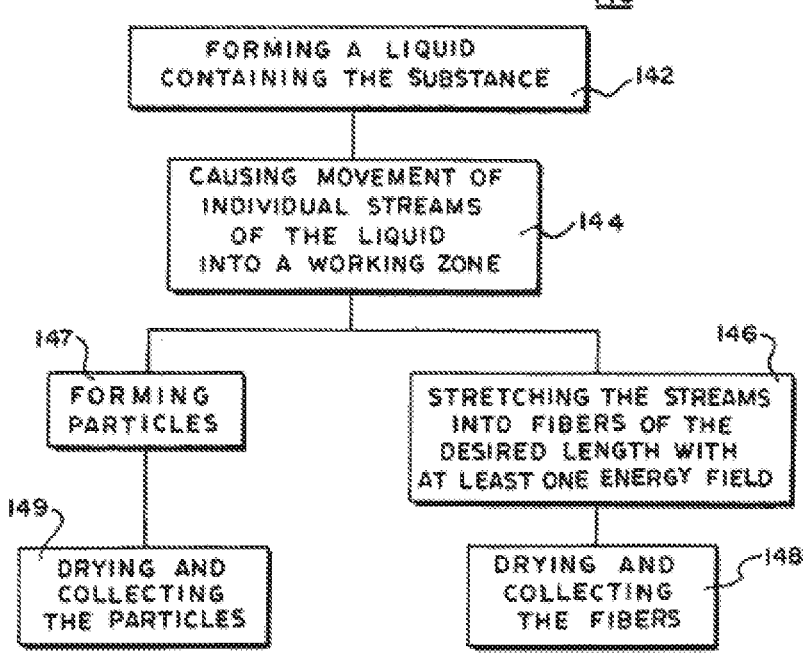
FIG. 7 is an embodiment of a flow diagram of a method forming particles or fibers, according to the inventive concepts disclosed herein.

In general, the flow diagram of FIG. 1 depicts an overview of methods of the present disclosure. For example, step (1) may include determining an appropriate feedstock material for an appropriate nanotechnology application including, but not limited to, nanomedicine, nano-suspensions including colloids, nanopillars, tissue engineering, drug delivery, biological labels, semiconductor fabrication, nanotube fabrication, nanowire fabrication, nano-fuels, bio-detection of pathogens, probing of DNA structure, tumor destruction, MRI contrast enhancement, other nanoscale applications, or combinations thereof; step (2) may include, but is not limited to, determining particle/fiber size, reactivity, volatility, reaction constants, viscosity (dynamic and/or kinematic), feedstock type (e.g., Newtonian, non-Newtonian, etc.), flow type (e.g., laminar or turbulent), pre-heat temperatures, Sherwood number, one or more dimensionless numbers (e.g., diffusion coefficient, etc.), flash point, dewpoint, bubble-point, density, lability, and/or combinations thereof; step (3) may include determining a propellant (e.g., air) based on the feedstock characteristics (e.g., if the feedstock is highly reactive, a relatively inert propellant, such as helium (He), argon (Ar), neon (Ne), krypton (Kr), xenon (Xe), radon (Rn), Nitrogen (N2), may be selected); step (4) may include determining the feedstock material and propellant combined characteristics including, but not limited to, rates of reaction, rates of separation, rates of dilution, rates of diffusion, rates of absorption, rates of adsorption, required purity levels, thermodynamic properties, phase equilibria and/or ratios (e.g., K-values), vapor pressure, entropy of reactions, heat transfer, fugacity or partial fugacities, respective dipole moments, rates of drying, rates of pervaporation for azeotropic mixtures, mass balances, mole balances, lability, volatility, hydrophilic-lipophilic balance (HLB Number), immiscibility, viscosity, and/or combinations thereof; step (5) may include determining a delivery mechanism and a distribution mechanism based on the characteristics determined in steps (1)-(4) (e.g., determining dimensions of delivery mechanism/means, determining whether fluid drilling with an auger, low pressure pump, capillary forces, and/or combinations thereof is delivery mechanism, and determining dimensions and/or what type of fixture and/or nozzle should be incorporated); step (6) may include determining and configuring an appropriate applicator, vehicle, or fixture to provide delivery characteristics (e.g., biological vector, polymer, liposome, nanocrystal, nano-vesicle, Ormosil nanoparticle, nanoemulsion, electrolyte or electrodes in electrodeposition, nanoparticle probe, or combinations thereof), that is configured or capable of providing desired interactions, reactivity, energy, and/or combinations thereof, which may be determined using appropriate relationships and/or functions (e.g., Nernst-Haskell equation, Geankoplis or Stokes-Einstein diffusivity equation, Wilke-Chang equation, Hayduk and Minhas equation, Fuller-Schettler-Giddings equations and empirical constants, Bernoulli's equation, friction heating terms, Reynolds number(s), friction factor for turbulent and/or laminar flow, Newton's law, Fick's Second Law equation, Ostwald-de Waele equation, Wilson's Equation, the non-random two-liquid (NRTL) model, the universal quasichemical (UNIQUAC) model, the UNIQUAC functional-group activity coefficients (UNIFAC) method/model, the Predictive Soave-Redlich-Kwong (PSRK) model, an electrolyte solution model, a polymer solution model, the Kremser equation, a McCabe-Thiele model/diagram, stage efficiency or number of stage models, an O'Connell correlation, a Hunter-Nash equilibrium method, an Emister/Lockhart/Leggett correlation, pressure drop model, a Fenske-Underwood-Gilland (FUG) method, or combinations thereof); and step (7) includes performing the desired application (e.g., drug delivery, biological labeling, semiconductor fabrication, nanotube fabrication, nanowire fabrication, bio-detection of pathogens, probing of DNA structure, tumor destruction, MRI contrast enhancement, etc.).

It is noted that at least some the steps above are not performed sequentially, but may be done in different orders or overlapping with another step. For example, some determinations of delivery mechanisms may be based substantially on feedstock characteristics determined in step (2). For instance, a feedstock determined to have micro-particles may enable a determination that needle-like pathways of the fixture should be increased in diameter for developing an appropriate distribution mechanism. Nevertheless, if a feedstock is determined to be volatile or labile, then one may need to know the propellant or its characteristics before determining an appropriate delivery and/or distribution mechanism. For instance, if the feedstock is determined to be an emulsified fuel or an ingredient of such, and the propellant is determined to be air and/or water, then the characteristics of the propellant (e.g., moisture content) may be required before being able to determine the appropriate delivery mechanism and/or distribution mechanism. Further, if an auger is the determined delivery mechanism, this may affect the determination of a propellant. For instance if the auger may only obtain a specific range of flow rates for delivery, then a low viscosity propellant may be determined as necessary to provide a sufficient constructive flow rate in order to obtain the overall extrusion or ligament formation flow rate.

Flow diagrams providing additional detail for steps and sub-steps of the flow diagram of FIG. 1 are provided in FIGS. 2-6.

Referring again to FIG. 1, in step (1), a nanotechnology application is determined. For example, the nanotechnology application determined may include an application and/or technique for forming a medicinal or medicated mat. In the nanotechnology industry, electrospinners, spray dryers, charged collectors, or applicators and distribution means may result in fibers or particles for distribution in a desired pattern.

In step (2) of an exemplary embodiment of a method disclosed herein, one or more characteristics of the feedstock or a feedstock material/ingredient are determined. For example, the feedstock may include ingredients, components, or particles that are labile. Feedstock materials that are labile must be delivered and/or distributed with precision and care. For example, a colloidal suspension or nanoemulsion may provide a better ligament for stretching to form fibers if it remains in a water/oil (W/O) emulsion, oil/water (O/W) emulsion, or water-oil-water (WOW or double) emulsion form until application of the electric potential or electric charge. During the preparation of the emulsion (e.g., with chitosan, in some embodiments, as an ingredient), an emulsifier or emulsifying agent having a viscosity of about 390 cP (e.g., at 50° C.) may need to be added (e.g., vitamin E—D-α-Tocopherol polyethylene glycol succinate (TPGS), with an HLB of about 13) and mixed with care. By way of another example, a propellant (e.g., heated air or gas) may contain moisture, affecting the lability of the emulsion. If the propellant contains a high moisture content (e.g., 0.015-0.055 kg/m$^3$), then contact with the labile ingredient may need to be minimized, a different propellant used, or the propellant may need to be heated and/or cooled (e.g., evaporation or condensation) prior to contact with the labile ingredient.

In an exemplary embodiment, a feedstock characteristic is determined including a determination that a feedstock material has a high viscosity or of a medium viscosity. For example, a kinematic viscosity (at approximately 20-25° C.) of chitosan may be from 1000 to 2000 (e.g., 1050) cPs, which may vary depending on water content of the chitosan (e.g., 1050 cPs for a 6% water content in 1% acetic acid at approximately 20° C.).

In some embodiments, the determination that a feedstock includes a high- or medium-viscosity fluid may include a determination that the feedstock should include an amphiphile. For example, the feedstock may be intended for a W/O or a WOW application and as such may require the addition of a surfactant, emulsifier, and/or a wetting agent. In some embodiments, the surfactant includes, but is not limited to, a gemini (e.g., double tailed surfactants), a viscoelastic, or a non-migratory surfactant. For example, the surfactant may include a glycoside, a glucoside (e.g., lauryl glucoside), an ether (e.g., octaethyleneglycol mono n-dodecyl ether), or combinations thereof. In some embodiments, the emulsifier includes xanthan gum (XG).

In some embodiments, the amphiphile is anionic. In other embodiments, the amphiphile is cationic. For example, the amphiphile may include, cetylpyridinium chloride (CPC), or a salt thereof. In other embodiments, the amphiphile is zwitterionic. For example, the amphiphile may include lecithin.

In some embodiments, the determination that a feedstock includes or should include a high- or medium-viscosity fluid includes a determination that a feedstock includes a glycerol soluble compound. For example, the feedstock may include ethers, low molecular weight alcohols, and combinations thereof.

In an exemplary embodiment, determining feedstock characteristics may include a determination that an ingredient of the feedstock does not mix well with another feedstock material/ingredient or with a propellant. For example, an emulsion may be termed a dispersion of two or more immiscible liquids in the presence of a stabilizing compound (e.g., emulsifier) and a fuel application may involve the delivery and/or distributing of one or more emulsions.

In an exemplary embodiment a feedstock characteristic is determined including a feedstock material consisting of particles having a specific size. For example, nanoparticles may be within the size range of 1 to 100 nm. By way of another example, micro-particles may be within the size range of 1 to 1000 micrometers (μm). For instance, a mean particle diameter may be determined using a dynamic light scattering (DLS) microscope, a scanning electron microscope (SEM), or a transmission electron microscope (TEM), and a surface area determined using Brunauer-Emmett-Teller (BET) analysis.

In an exemplary embodiment a feedstock characteristic is determined including a determination that the feedstock or an ingredient of the feedstock should be mixed via a batch or a continuous process. For example, a predetermined quantity of chitosan may be mixed as a batch for an electrodeposition process. In contrast, an electrospinning application may occur in a continuous manner, such that as long as ingredients are provided, the process does not stop.

In an exemplary embodiment, determining a feedstock characteristic may include determining that the feedstock material includes a non-Newtonian fluid that is represented by the Ostwald-de Waele equation and determining accompanying characteristics. For example, the feedstock material may include chitosan (or a derivative thereof) and a synthetic, water-soluble polymer (e.g., partially hydrolyzed polyacrylamide (HPAM)) dispersion having an n-parameter of approximately 0.7-1.14 and a K parameter of approximately 0.087-0.15 (kg/m·s2−n) at 20-25° C. (e.g., 0.1 M aqueous acid and 0.1 M acqueous acetic acid/0.2 M NaCl). It is noted that other similar parameters may be obtained based on composition and repeated testing. In these embodiments, the nanotechnology application may include a nanomedicine application.

In an exemplary embodiment, determining a feedstock characteristic may include determining costs or ease of production of one or more ingredients of the feedstock material. For example, a first ingredient (e.g., natural) may possess similar characteristics as a second ingredient (e.g., synthetic), but may cost more or may be more difficult to obtain. In such situations, often the second ingredient is used as opposed to the first to minimize overall costs, however, this may depend on other factors (e.g., environmental conditions, EPA regulations, etc.).

In an exemplary embodiment, determining a feedstock characteristic may include determining a desired flow rate of the feedstock material. For example, feedstock materials may have a limit as to the amount of mixing that can occur during transport through a circular pipe or tube, thus mixing characteristics are determined to limit the length of pipe/tube used during transport. By way of another example, the feedstock material may need to be mixed further during flow from a hopper to a distribution mechanism. In either example, a desired flow rate of the feedstock material and mixing characteristics may be determined with respect to turbulent flow through a circular pipe according to a dispersion coefficient, such as in the relationship below:

$$D_{turbulent} = 3.57 \sqrt{f} VD$$

where $D_{turbulent}$ is a dispersion coefficient (e.g., axial dispersion coefficient), f is a friction factor, V is velocity (e.g., average velocity of the fluid), and D is diameter (e.g., pipe/tube diameter). In this regard, the flow rate may be determined using a second relationship (e.g., Bernoulli's Equation or form thereof).

In an exemplary embodiment, determining a feedstock characteristic may include determining a combined characteristic of feedstock ingredients. For example, a combined characteristic may include a type, size, and composition of a micelle. By way of another example, the Feedstock may include one or more reactants, $r_A, r_B, \ldots r_N$, and in some embodiments it may be desirable to combine the one or more reactants (e.g., in the delivery mechanism, or a portion thereof) with each other prior to being propelled out a distribution mechanism by the propellant so as to induce a chemical reaction and an emission (e.g., spray) having a specific concentration of a reactant and/or product. In some embodiments, it may be necessary to determine a mole balance of the chemical reaction, which for a steady state, tubular reactor (e.g., delivery tube) may be determined as follows:

$$\frac{dF_j}{dV} = r_j$$

It may also be necessary to determine at what point reactants are combined in order to produce a decomposition, combination, or isomerization of a reactant. To determine this point, a chemical reaction volume, $V_1$, necessary for the decomposition, combination, or isomerization of a particular reactant, rA, may be determined in order to ascertain the point at which reactants are combined. For example, the chemical reaction volume, $V_1$, may be determined as follows:

$$V_1 = \int_{F_{A0}}^{F_{A1}} \frac{dF_A}{r_A} = \int_{F_{A1}}^{F_{A0}} \frac{dF_A}{-r_A}$$

where $V_1$ may be characterized as a volume necessary to carry out a reaction such that an incoming flow rate, $F_{A0}$, is reduced to a specific value, $F_{A1}$, which by the nature of a chemical reaction, is also the volume necessary for a molar flow rate for generating a product (e.g., isomer, etc.).

In step (3) of an exemplary embodiment of a method disclosed herein, a propellant is selected and/or determined based on a feedstock characteristic determined in step (1). For example, selecting a propellant includes selecting the propellant from at least one of an inert gas, air, nitrogen ($N_2$), a low viscosity fluid, a miscible ingredient, an immiscible ingredient, and combinations thereof. For instance, if the feedstock characteristic determined includes a determination that the feedstock includes a volatile or labile ingredient, the propellant may be selected from as an inert gas or as nitrogen.

In an exemplary embodiment selecting the propellant may include determining a flow rate of the propellant or how viscous a propellant may be based on a determined characteristic of the feedstock. For example, if the feedstock is determined as having a first velocity that is smaller than a distribution velocity (e.g., a rate at which the feedstock combined with a propellant leaves a nozzle), the propellant may need to have a specific velocity and/or viscosity, or be within a range of velocities and/or viscosities, to make up the difference and propel the feedstock to obtain the distribution velocity. For instance, the propellant is generally provided at low energy via one or more low pressures (e.g., 1-15 psi), thus the propellant may be required to have a specific velocity and/or viscosity or be within a range of velocities and/or viscosities (e.g., 0.01 to 1 cP) in order to make up the difference and cause the feedstock to reach the distribution velocity, which velocity and/or viscosity (or range thereof) may be determined using Reynolds number(s), friction factor(s), Bernoulli's equation, and/or combinations thereof.

Figure 9:
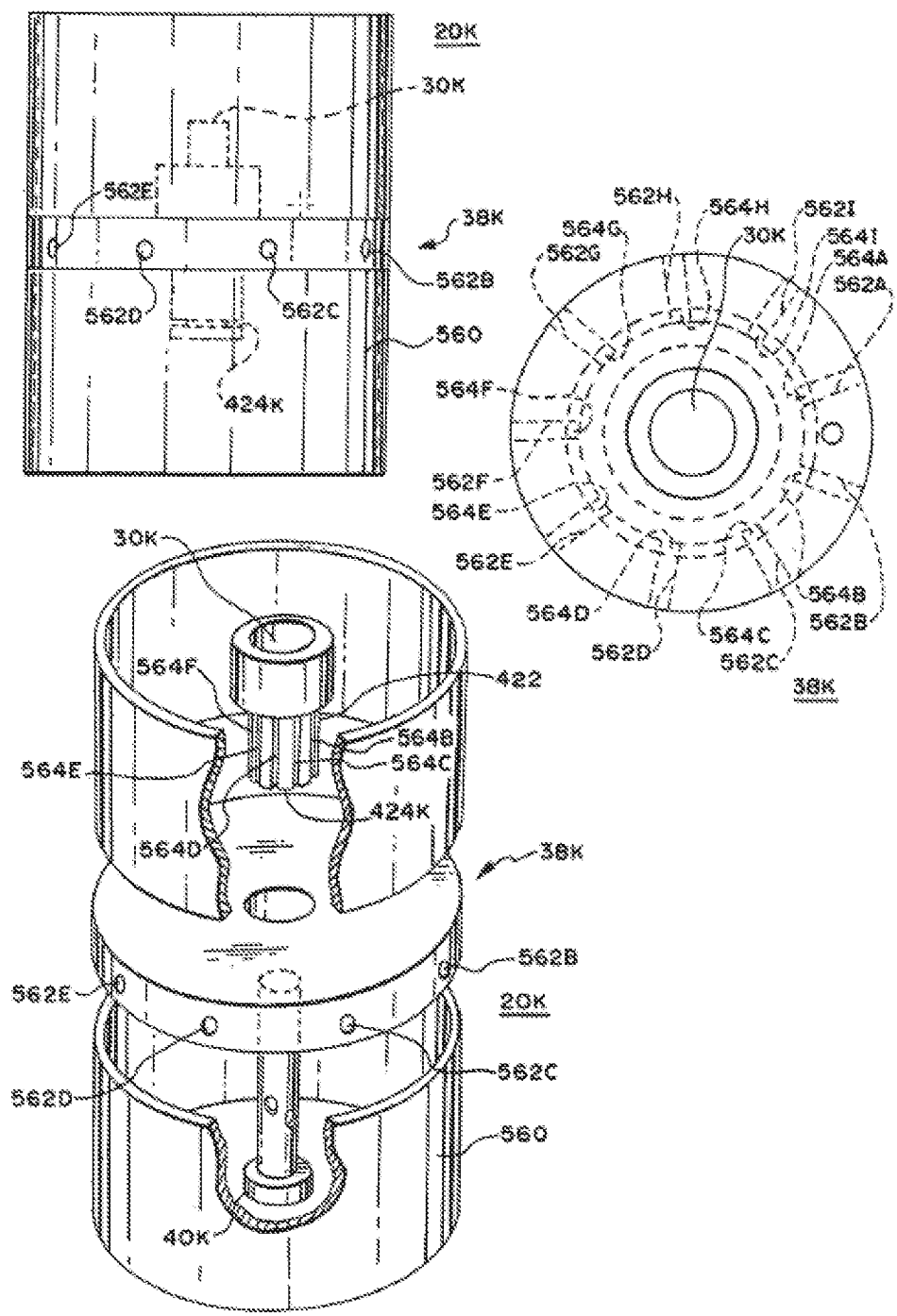
FIG. 9 is an embodiment of a distribution mechanism, according to the inventive concepts disclosed herein.
Figure 10:
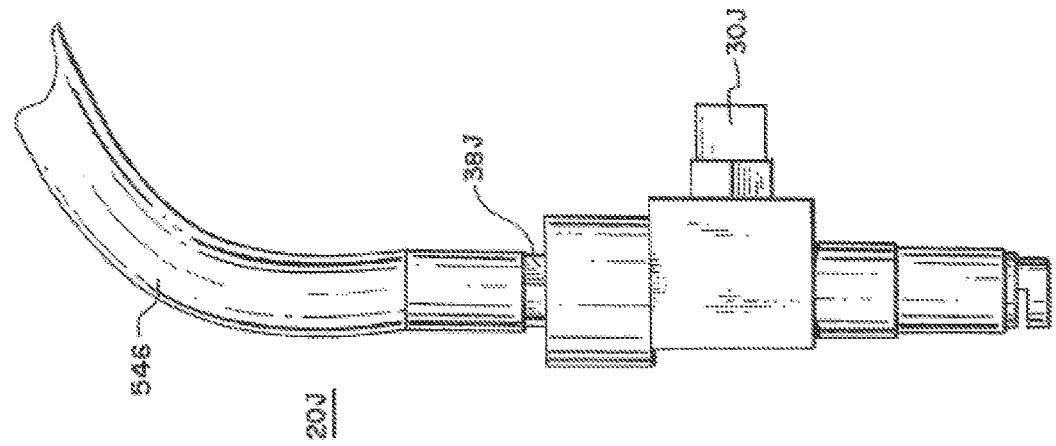
FIG. 10 is an embodiment of a distribution mechanism, according to the inventive concepts disclosed herein.
Figure 10:
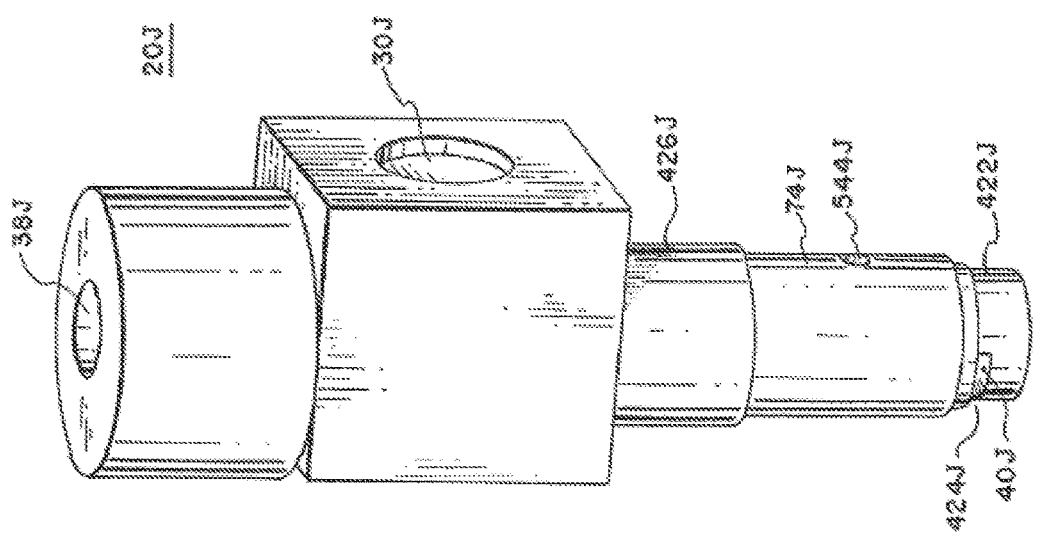
Figure 11:
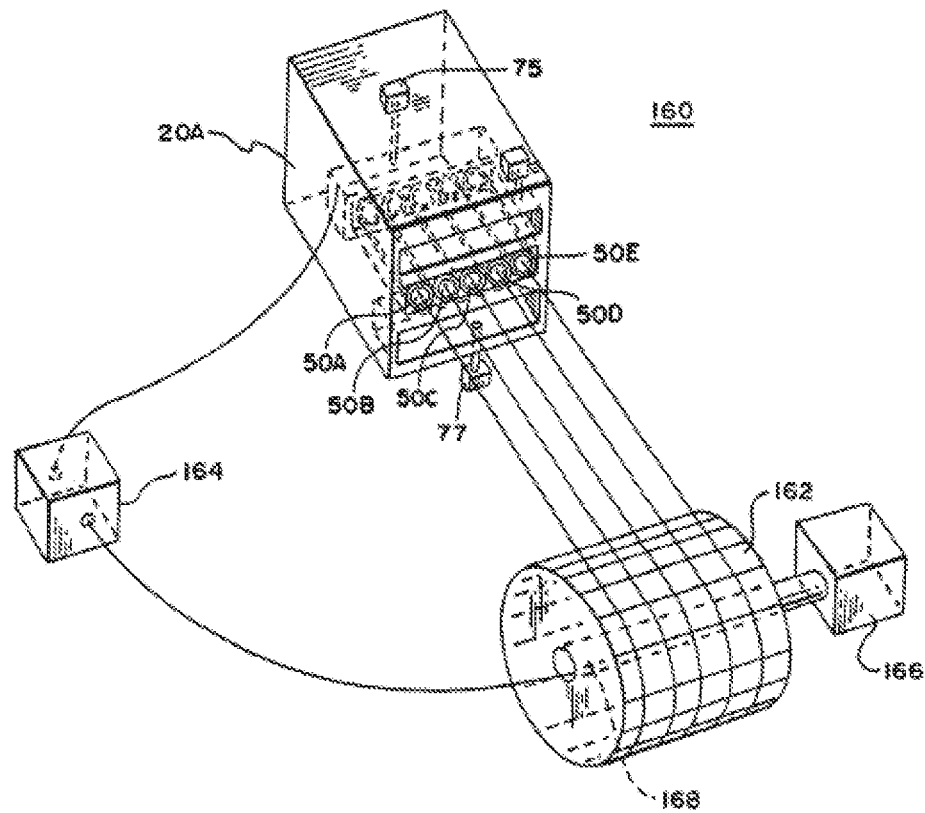
FIG. 11 is an embodiment of a distribution mechanism, according to the inventive concepts disclosed herein.
Figure 11:
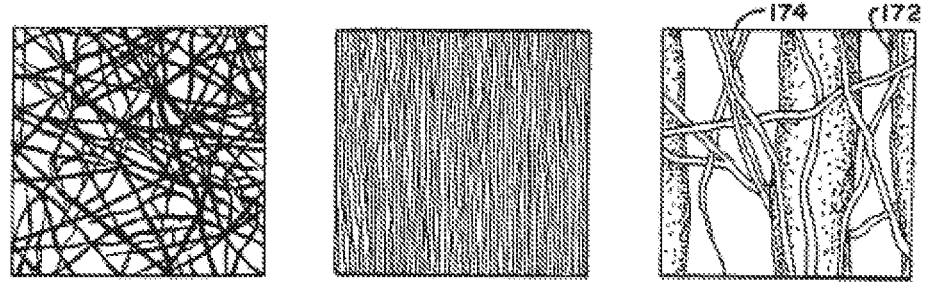
Figure 12:
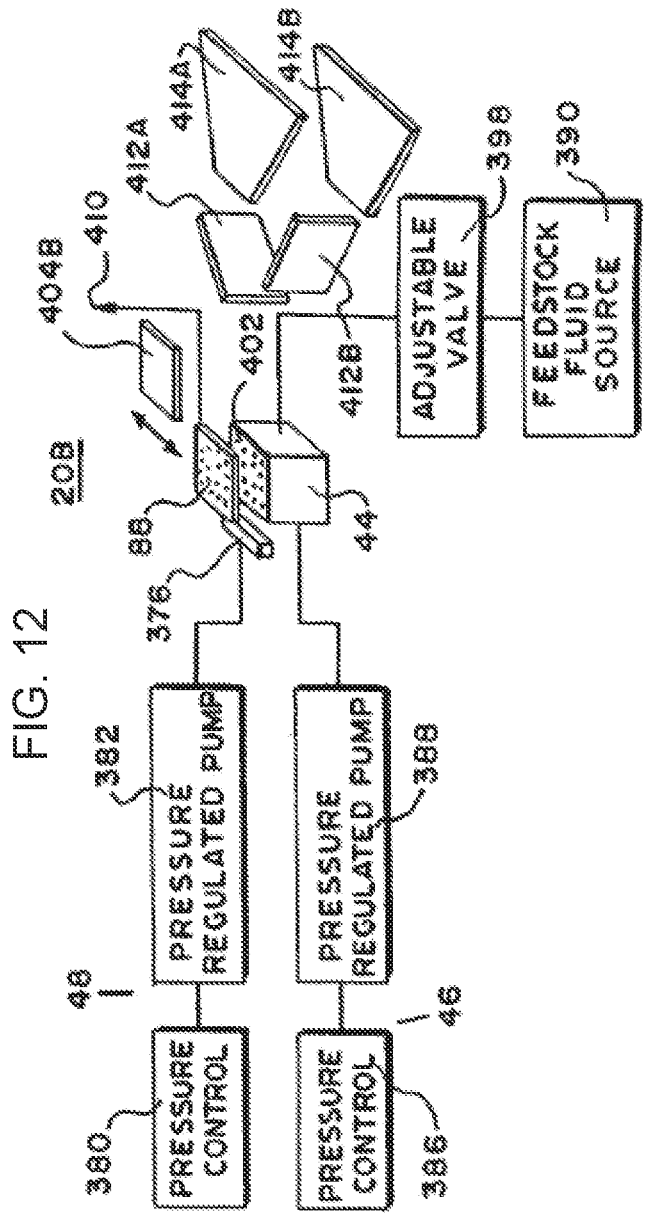
FIG. 12 is an embodiment of a distribution mechanism, according to the inventive concepts disclosed herein.

In an exemplary embodiment, selecting the propellant based on a characteristic of the feedstock may include determining an allowable moisture content of the feedstock, and thus an allowable moisture content of the propellant. For example, some chitosan mixtures have increased effectiveness (e.g., increased preservation or reduced degradation) when water content is reduced and/or minimized. In this regard, if a chitosan mixture is used and it already contains a maximum, or high, water content for overall effectiveness of the fibers in a nanomedicine application (e.g., formation of a weaved or medicinal mat), then the propellant may need to be selected as nitrogen or carbon dioxide instead of air, depending on the water content of the air. In other embodiments, the air undergoes a condensation or evaporation process to remove the moisture from the air.

In step (4) of an exemplary embodiment of a method disclosed herein, a combined characteristic or a combining characteristic is determined based on bringing the feedstock and the propellant into contact with each other. For example, the combining characteristic or combined characteristic may include one or more of the following: combined flow rate, combined viscosity, resulting temperature upon combination, whether or not mixing is desired as a result of the combination, any resulting reactions or rates of reaction resulting from the combining, an angle of combination (e.g., angle at which propellant contacts the feedstock), and a resultant energy of the combination.

In step (5) of an exemplary embodiment of a method disclosed herein, a delivery mechanism and a distribution mechanism is selected and/or determined. For example, a delivery mechanism may be selected from one or more of the following: an auger; a low pressure pump, blower, or compressor; needle-like columns; capillary forces; first two opposing plates positioned at an angle to a second two opposing plates; an electric charge; and combinations thereof. For instance, the delivery mechanism may be selected as a fixture from the delivery mechanisms depicted in FIGS. 9-12. In FIG. 9, a fixture 20K adapted to mix a plurality of liquids or particles without regard as to whether the liquids are viscous or mobile is shown. The fixture 20K includes a mixing chamber 560, a kinetic energy inlet 30K, an inlet 38K for a plurality of fluids or particles and an outlet 424K. The fixture 20K receives a plurality of fluids which may be of any viscosity or may be mobile or may consist of particles or emulsions or other combinations in the inlet member 38K while receiving air or other kinetic energy fluid through the kinetic energy inlet 30K. The outlet 424K emits gaseous clouds of droplets or fine particles made up of the different inlets which are mixed together in the mixing chamber 560. From the mixing chamber 560 they may flow to a nozzle for spraying or may flow to a combustion device for burning or any other location where the mixture is affective. The inlet member 38K includes a plurality of openings leading inwardly 562A-562K with openings 562B-562E. In FIG. 9, the fixture 20K showing the kinetic energy inlet 30K and the bottom plate 40K of the outlet opening 424K is further shown. The opening 424K extends 360 degrees around the longitudinal central axis. However, it can be any number of degrees or any of the fixtures since that merely determines the size of dimension the liquid and this is the amount of liquid inputted by the surface force. Thus the size of the droplets and the range of spreading and can be tailored to an individual application. The inlet opening of the inlet 38K extends to channels or slots circumferentially spaced from each other in the thickness control insert 422. The recessed cylinder of the thickness control insert 422 is cylindrical with longitudinal channels extending downwardly to the outlet 424K so that liquid flowing through the channels from the inlets to connect with a corresponding one of the channels 564A-564K. The fluid or particles are channeled through the channels down to the outlet and against the bottom plate 40K. The thickness insert may be adjusted as to its distance between the bottom plate 40K to determine the thickness of fluid and thus affect the size of the droplets being emitted. In FIG. 9, the member 38K showing the inlet channels 562A-562I and the corresponding downward slots 564A-564I is further shown. As shown in FIG. 9, the different fluids flow downwardly to the outlet where they are impacted by the kinetic energy fluid flowing through the kinetic energy inlet 30K and thus form a cloud of droplets to be mixed in the mixing chamber 560. In FIG. 10, there is shown a perspective view of another embodiment of fixture 20J having a feed stock inlet opening 38J, a kinetic energy fluid inlet 30J and an outlet opening 424J having an opening distance controlled by the location of the insert 422J and the outlet cylinder 74J. A threaded opening receives a screw for holding the distance between the insert 426J and the outlet cylinder 74J which determines the size of the opening 424J and thus will affect droplet size. In FIG. 10, there is also shown an elevational view of the fixture 20J with the feed stock inlet connected to a hose 546 for receiving an agricultural input and applying it to the feed stock inlet opening 38J of the fixture 20J. The air line receives a nipple from the boom to receive pressurized air so as to provide a spray to crops or the like. In FIG. 11, there is shown an apparatus 160 of forming continuous fibers having a fixture 20A, a collector 162, a source of high potential 164, a motor 166 for driving the drum assembly and that serves as a collector 162. The fixture 20A receives two kinetic energy fluids through the regulators 75 and 77 to contact the feedstock material. The feedstock material is being extruded from needle openings 50A-50E onto the collector 162 which is rotated by the motor 166 while a high potential electrical difference is applied between the needles 50A-50E and the collector 162 to further stretch and draw the fibers. In the preferred embodiment, the fibers are drawn into nanofibers 172, 174. For example, in one embodiment, the feedstock material leaving the needles 50A-50D is fed at a rate between and two and seven microliters per minute through the regulator 75. In FIG. 12, there is shown a simplified block and schematic diagram of another embodiment of fixture 20B having a film or sheet forming container 44, a film and sheet forming fluid source 46, a drop and particle moving fluid source 48, a feedstock fluid source 390, an adjustable valve 398 and a drop former 88. The feedstock fluid source 390 and the film and sheet forming fluid source 46 communicate with the film or sheet forming container 44 to supply feedstock fluid and a gas thereto. The top surface of the film or sheet forming container 44 includes a plurality of perforations 402 and an adjustable perforation cover plate 404B may be moved to cover a portion of the perforations 402 and thus adjust the amount of fluid being formed into bubbles and eventually into drops and/or particles. The feedstock material selected for this embodiment and the gas pressure from the film and sheet forming fluid source 46 must be such that the gas pressure will form bubbles by applying pressure to the feedstock material but not burst the bubbles. The surface tension of the feedstock material is sufficiently great to maintain integrity as a film or sheet under the pressure supplied from the film or sheet forming fluid source 46. The combination of pressure and feedstock material varies from application to application.

By way of another example, a distribution mechanism may be selected from one or more of the following: a nozzle attached directly to a delivery tube; an atomizing spray fixture; multiple sets and/or configurations of nozzles; an air-assist nozzle; a nozzle with a separator; an opening between a plate and a spray fixture; and combinations thereof. For instance, the distribution mechanism may be selected from fixtures depicted in U.S. Pat. No. 9,148,994, issued on Oct. 6, 2015, filed Nov. 12, 2012, by John Alvin Eastin, et al., which is incorporated herein by reference in its entirety.

In step (6) of an exemplary embodiment of a method disclosed herein, an applicator is configured for the spray application selected and the characteristics determined. For example, the type of applicator may be one of a charged collector, an electrospinner, a spray dryer, or a combination thereof. The delivery means (e.g., tube, pipe, slit, corrugated tubing, etc.), length, geometry, etc., may be determined using an equation/relationship including but not limited to, Bernoulli's equation, Reynolds No., friction factors, etc. The Application environment may also be determined, including but not limited to, a humidity, pressure, ambient temperature, air flow, ventilation, and combinations thereof. A determination may also be made as to whether a pre-existing applicator (e.g., charged collector) may be retrofitted. Flow rates and/or speeds of the applicator and/or related components (e.g., rotating drum, conveyor belt, etc.) may also be determined in order to configure the applicator for the desired application (e.g., electrospinning, nano-fiber extrusion, etc.). The application characteristics (e.g., drop patterns, fibers, mists, etc.) may also be determined at this step.

In step (7), the application is performed according to the various determinations made. For example, the methods and apparatuses disclosed herein may be useful for nanomedicine applications including a fiber carrier application. For example, a charged collector apparatus may be incorporated with a delivery mechanism and/or a distribution mechanism as disclosed herein to collect particles and/or fibers for other uses (e.g., colloidal suspension, nanoemulsion, medicinal mat, etc.).

It is noted that while some of the inventive concepts may be discussed with respect to an electrospinning application and/or process, the inventive concepts will be recognized by those skilled in the art to be applicable to other applications and/or processes (e.g., biological labeling, chitosan solution formation, etc.). For example, referring now to FIG. 7, there is shown a flow diagram of a process 140 for forming fibers comprising the step 142 of forming a liquid containing the substance to be formed into fibers or powders, the step 144 of causing movement of individual streams of the liquid into a working zone, the step 146 of stretching the streams into fibers of the desired length with at least one energy field and the step 148 of drying and collecting the fibers or the alternate steps 147 and 149 of forming particles such as powder and drying and collecting the particles. Some materials are difficult to put into a form which can be further formed into small fibers. For example silica and chitosan and many metal ceramic compositions are useful if they are put into a nano-fiber or nanoparticle form but it is difficult to get them into a liquid form and then use prior art processes to form nano-fibers. In this invention, once the desired substances are put into a liquid, they can be moved as indicated by the step 144 into a working zone by the delivery mechanism (e.g., FIG. 11). While in the working zone, streams of the liquid can be stretched to the desired diameter using an energy field or plurality of energy fields. In the preferred embodiment, the liquid includes solvent which evaporates resulting in solid fiber or particles. For example the delivery mechanism of FIG. 11 provides a kinetic energy fluid as one field and another kinetic energy fluid as another field which stretches the streams because they are moving at different velocities, one on one side of the stream and the other on another side. When the streams are at the right desired diameter, they are dried and can be collected by known processes such as electrospinning or a charged collector as shown in step 148. These particles and fibers may be used as carriers for other chemicals such as agricultural inputs.

Figure 8:
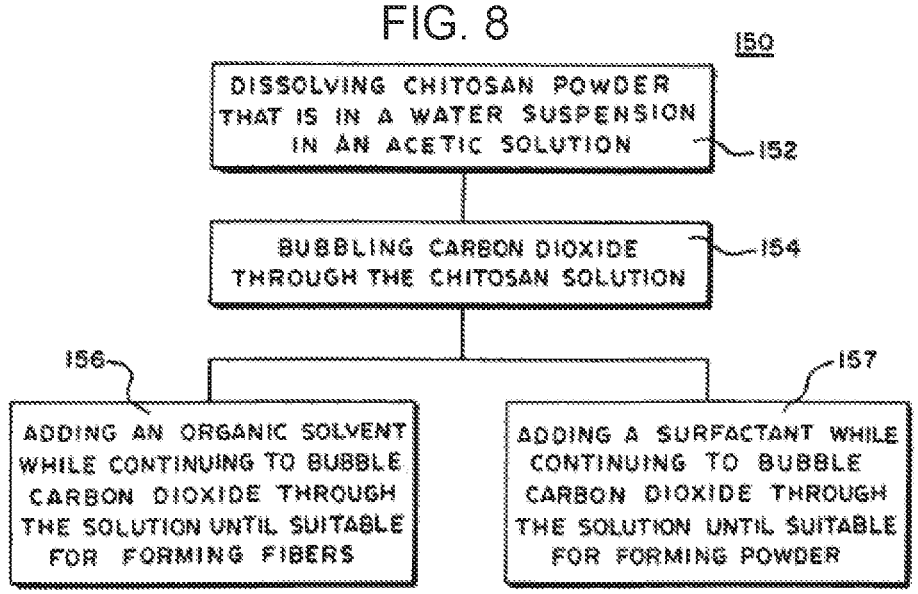
FIG. 8 is an embodiment of a flow diagram of a method forming a chitosan solution, according to the inventive concepts disclosed herein.

In FIG. 8, there is shown a process 150 for forming one important material, chitosan, into a liquid state so as to form chitosan fibers or powders which are useful for many purposes. For example chitosan fibers can be used in many pharmaceutical applications such as drug delivery and controlled release and in medical technology such as wound and burn dressings or surgical treatment, dermatitis and fungal infections, contact lens, bacteriostat and fungistat and bone disease, biotechnology applications such as membranes, biocatalysts, enzyme immobilization, protein separation, cell immobilization, food products, preservatives, fat absorption animal feed additives, metal-chelating processes such as absorption of transition metal ions such as copper, chromium, lead, silver and so on, agricultural products such as timed-release, seed coating, foliar application and paper products. However, there are difficulties in forming a liquid containing chitosan that would be suitable for the making of fibers. One difficulty is that most known solutions are more conductive than desirable and have a higher viscosity than desirable for the prior art methods of forming fibers. An improved method of putting chitosan into a liquid state is shown in FIG. 8.

The process of FIG. 8 for putting chitosan into a liquid state suitable for the forming of fibers, thin films, mats or powders includes the step 152 of dissolving chitosan powder in a water in an acidic solution such as a acetic acid solution, the step of 154 of bubbling carbon dioxide through the chitosan solution, the step 156 of adding an organic solvent while continuing to bubble carbon dioxide through the solution until it is suitable for making a desired solution that can be used to make fibers or powders or the step 157 of adding a surfactant while continuing to bubble carbon dioxide through the solution until the solution is suitable for forming powder. While it is known that acetic acid can be displaced by bubbling carbon dioxide through the acetic acid solution, this has not been applied to chitosan solutions. While carbonic acid ($H_2CO_3$, on $CO_2$ solubilization) has a lower pK than acetic acid, it is mere mass action imposed by continuous feeding of the former that facilitates removal of the organic acid from the aqueous environment. The use of $CO_2$ instead of an inert gas has the synergistic effect of stabilizing a pH below five, which is critical to maintaining chitosan in solution. However, the $CO_2$ bubbling by itself leads to chitosan precipitation by saturation as the water and acid is removed. This problem is avoided by adding solvent. Superior results in avoiding precipitation of chitosan have been obtained by replacing the lost ingredients with ethanol, thus synergistically lowering the surface tension, viscosity and conductivity of the solution, which is required for making fibers. If an alcohol is added without bubbling carbon dioxide through the solution, the solution may form a gel with only the addition of a small amount of alcohol.

The chitosan-water-$CO_2$-ethanol solution is difficult to spin in this form. However, it has been found that addition of as little as 0.25 wt. % or preferably 1.25 ml. % poly (ethylene oxide) (PEO) is sufficient to markedly improve fiber formation using prior art spinning techniques with temperature and voltage control and the addition of surfactant improves the formation of powders. The use of the two kinetic energy fluids on different sides of a compatibly-selected feedstock material also permits the formation of satisfactory fibers without electrospinning and the formation of longer fibers using the above solution and electrospinning Evaporation of a small amount of ethanol during the time-of-flight of the charged liquid filaments from the delivery capillary to the collector electrode is all it takes to induce solidification. Interestingly, while the dominant chitosan weight fraction in the fibers is insoluble in water, washing the fibrous deposits with de-ionized water lowers the PEO content below its starting value. More specifically, in one embodiment, solutions of chitosan requiring very small amounts of plasticizers such as poly(ethylene) oxide, or no plasticizer agents at all, are prepared by dissolution of chitosan in carboxylic or mineral acid aqueous solutions, followed by total or partial displacement of the acid with carbon dioxide bubbling, and addition of controlled amounts of ethanol. With the aid of electrohydrodynamic processing of the solution formulation, fibers and particles with diameters in the micron and submicron range are produced. The chitosan solution formulation also affords processing into thin films, given its lower surface tension than other formulations based on water and carboxylic and/or mineral acids.

In some embodiments, the delivery mechanism may utilize low pressures to deliver a lipophilic, high viscosity fluid to encapsulate (e.g., perform encapsulation) a particle.

In some embodiments, the distribution mechanism may include a nozzle. In embodiments, the nozzle may include a shearing knife and propellant (e.g., air flow directed at the nozzle) to remove a portion of the high viscosity fluid from a tip of the nozzle.

In embodiments, a fluid drilling delivery mechanism is utilized, which may include one or more augers having threads designed for low pressure delivery of a feedstock material via a shearing surface of the thread for delivery to a distribution mechanism.

Figure 13:
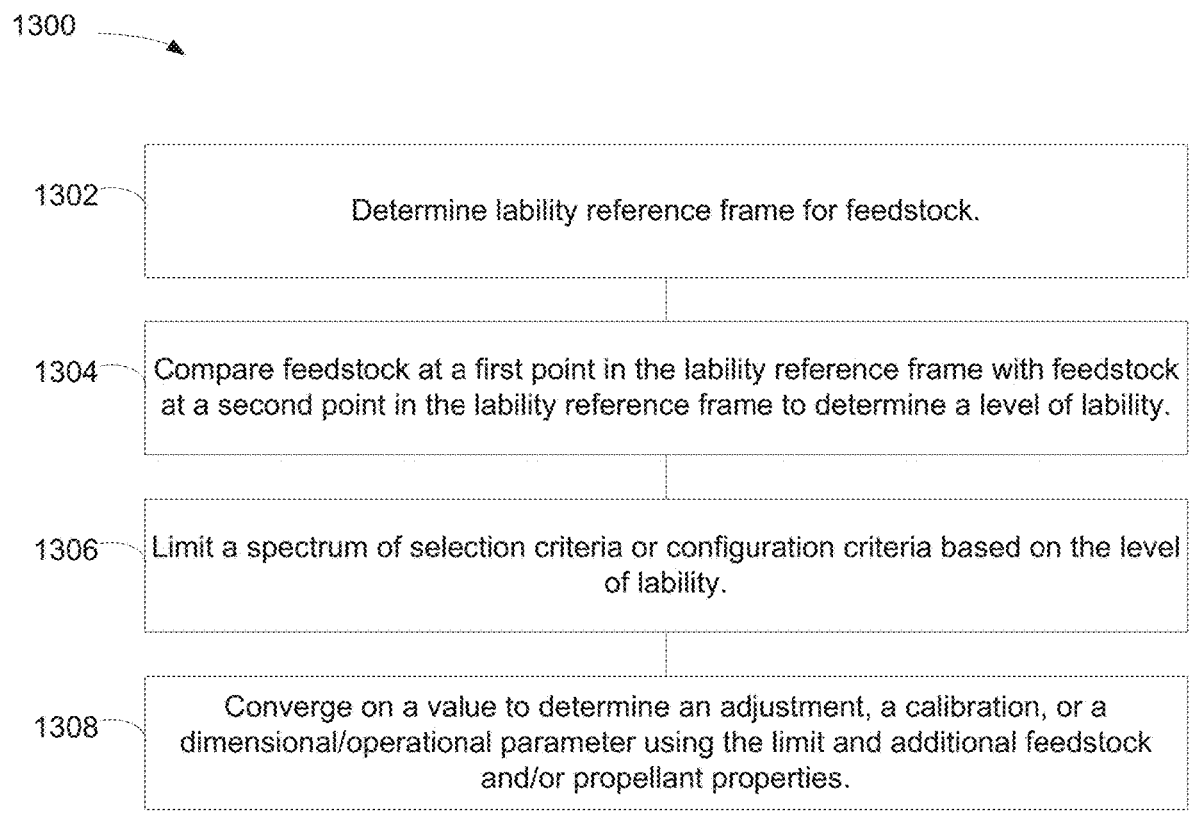
FIG. 13 is an embodiment of a flow diagram of a method for labile-based delivery and distribution for nanotechnology applications, according to the inventive concepts disclosed herein.

Referring now to FIG. 13 an exemplary embodiment of a method 1300 according to the inventive concepts disclosed herein may include one or more of the following steps. For example, the method 1300 may be a method for labile-based emission, extrusion, delivery, and distribution for nanotechnology applications.

Step 1302 may include determining a lability reference frame for feedstock. For example, the lability reference frame may include, but is not limited to, lability with respect to pressure, temperature, pH, other reactants (e.g., chemical reactivity), an emulsion (e.g., how long feedstock stays as an emulsion-storage stability test using techniques such as the ASTM method and/or a separation index), a resistance to shear or tensile stress, kinematic effects, exposure time, emission form (e.g., drops, mists, fibers, nan-particles, etc.), a reference frame with respect to another element or compound (e.g., water-hydrophobic, hydrophilic, or amphiphilic; or fat-such as lipophilic), and intermolecular forces (e.g., has a bonded by a covalent bond as opposed to bonding by Van der Waal's forces). For instance, a first lability reference frame may be pH used in the context of applying nanoemulsions for medicated or medicinal mats. For instance, if a first lability level of the nanoemulsion is determined at a pH of 4, a second lability level of the nanoemulsion may be determined a pH of 7 or 8, such that the second lability level (e.g., as determined by a lability characteristic such as % water separation) is greater than the first lability level. Multiple levels between the first lability level and the second lability level, inclusive, may be considered a lability reference frame.

In some embodiments, the lability reference frame is a combinational reference frame. For example, the lability reference frame may be based on a combination of two or more of pressure, temperature, salinity, pH, other reactants (e.g., chemical reactivity), a resistance to shear or tensile stress, kinematic effects, intermolecular forces. For instance, the lability level of a nanoemulsion incorporating a brine solution at a pH of 7 may be greater than the lability level of a nanemulsion using distilled water at a pH of 7. By way of another example, a mat (e.g., wound dressing) may be treated with a beneficial ingredient (e.g., antibiotic, coagulant, biological, etc.). In this regard, the combinational lability reference frame may include a combination of temperature, pH, and salinity associated with skin or tissue to which the medicated plant may be applied.

In some embodiments, the lability reference frame is determined for an as-applied feedstock. For example, the lability reference frame may be determined for feedstock ingredients as they are intended to be applied to fibers, woven particles, or combinations thereof. By way of another example, the lability reference frame may be determined for feedstock ingredients with respect to the emission form in which they are intended to be applied. For instance, the lability reference frame may include determining a lability level within the reference frame of fibers, drops, mists, extrusions, emulsions, and other distribution/emission forms. For instance, drops and mists may be more labile than hardened fibers, extrusions, and emulsions due to characteristics (e.g., exposed surface area, amount of unexposed ingredients, etc.) of the form in which they are emitted. In other embodiments, the lability reference frame is determined for an as-distributed feedstock. For example, one or more ingredients may be added to a hopper or a container for distribution from a fixture to a charged collector. In this regard, the lability reference frame may be determined with respect to the ingredients to be distributed, a propellant, an electric charge or potential of the collector, or combinations thereof.

In some embodiments, the lability reference frame is determined for a combined feedstock and propellant mixture. For example, an amino acid such as lysine may be an ingredient of a feedstock to be applied to fibers or particles of a nanotechnology application, and air or nitrogen may be used as a propellant to aid in the distribution, delivery, emission, or spray of the lysine to the fibers/particles.

A step 1304 may include comparing feedstock at a first point in the lability reference frame with feedstock at a second point in the lability reference frame to determine a level of lability. For example, an ingredient of the feedstock may be applied at a pH of 6-8 (e.g., average pH of nanoemulsion), such that the lability reference frame may be a pH reference frame. In this regard, the lability reference frame may have multiple points determined with respect to an ingredient of the feedstock. For instance, the lability reference frame may include pH points of approximately 1.5 to 11.0, such that comparing the feedstock at a first point in the lability reference frame with feedstock at a second point in the lability reference frame may include comparing a feedstock ingredient such as lysine at the as-applied pH level of approximately 6-8 to lysine in a solution/emulsion having a pH of approximately 5-6 in order to determine the level of lability of the feedstock ingredient. In this regard, the lysine at a pH of 6-8 may be categorized to a low lability level. In contrast, lysine at a pH of 5-6 may be compared to lysine in an emulsion having a pH of 6-8, and may be categorized to a high lability level. Categorical levels of lability may include, but are not limited, high lability, medium lability, and low lability.

In some embodiments, the level of lability may be determined by comparing a feedstock ingredient at a first combinational point in the lability reference frame with a second combinational point in the lability reference frame. For example, a first amino acid (e.g., lysine) may be applied to a mat or woven fibers, and a lability level may be a high lability level at a temperature of 20° C. and a moisture content of greater than approximately 0.01 kg/m³, a medium lability level at a temperature of 20° C. and a moisture content of approximately 0.003 kg/m³ (e.g., about 30% relative humidity) to 0.01 kg/m³, inclusive, and a low lability level at a temperature of 20° C. and a moisture content of less than approximately 0.003 kg/m³.

In some embodiments, geographical region with effects including moisture content and temperature may be accounted for when determining lability level. For example, a mat or woven fibers receiving a treatment or medication in a geographical region that has a relatively low moisture content (e.g., desert), may be associated with a feedstock having a different lability level than the same feedstock used for a similar mat receiving the same treatment or medication in a geographical region with relatively high moisture content (e.g., coastal region).

In some embodiments, determining the level of lability in Step 1304 may include determining that another feedstock ingredient is needed for the nanotechnology application. For example, if the lability reference frame is a water-based lability reference frame, and the level of lability of a feedstock ingredient is determined to be a high level of lability (e.g., hydrophilic), then the Step 1304 may include a determination that an emulsifying agent should be added as another feedstock ingredient.

A step 1306 may include limiting a spectrum of selection criteria of distribution mechanisms, delivery mechanisms, fixtures, applicators, applicator configurations, and combinations thereof for nanotechnology applications based on the level of lability determined in step 1304. For example, for a nanotechnology application such as mat/woven fiber treatment, a large number of applicators and/or fixtures may be available to perform the treatment/medication, where each applicator or fixture may be associated with its own selection criteria. In this regard, the level of lability within the specific lability reference frame may limit the selection criteria or configuration criteria sufficiently such that a particular applicator or a particular spray fixture may be chosen for the treatment/medication. For instance, a feedstock ingredient having a low level of lability within a viscosity lability reference frame (i.e., meaning the ingredient is highly viscous) may need to be mixed at a gaseous state, such that the lability reference frame and the feedstock characteristics (e.g., needing to be mixed in gaseous state) may limit the spectrum of selection criteria such that an atomizing spray fixture may be selected for the treatment/medication of the mat.

In some embodiments, the Step 1306 may include limiting a spectrum of configuration criteria based on the lability level. For example, an applicator such as a fluid drilling applicator may be selected based on the level of lability for the specific lability reference frame determined in Step 1304. For instance, the low-level lability ingredient within the viscosity lability reference frame (e.g., highly viscous ingredient), may be best delivered using a low pressure configuration, such as with an applicator that has an auger configuration like those used in fluid drilling applicators. By way of another example, a lability reference frame may be a combinational lability reference frame, wherein a lability level is determined with respect to at least three factors. The three factors may be chemical reactivity/structure, absorption rate, and metabolic interaction/conversion. In this regard, the lability level may be associated with a toxicity level or a toxicity lability reference frame such that specific nanotechnology applications may be eliminated based on the lability level of toxicity. For instance, if a substance is highly labile within a toxicity lability reference frame (i.e., where toxicity level and lability level are directly correlated), then nanotechnology applications such as biological labeling, encapsulation, mat/woven fiber treatment, or any application that may present a direct health hazard if the highly labile ingredients were introduced into a blood circulatory system, can be eliminated or limited. In other words, the selection criteria would be programmed logically to remove those nanotechnology applications from possible selections for the high-labile level ingredients. This may leave non-biological industrial nanotechnology applications as potential applications.

A step 1308 may include converging on an adjustment parameter, a calibration parameter, a dimensional parameter, an operational parameter, or combination thereof using the limits determined in Step 1306 and using additional feedstock properties. For example, the limit in Step 1306 may help select or configure a particular spray fixture for a specific nanotechnology application. Then, using an additional feedstock property such as a velocity of an extruded feedstock or a flow rate of a sprayed nanoparticle, an adjustment to a nozzle of the spray fixture or extrusion fixture may be converged upon. In this regard, a feedback controller (e.g., proportional-derivative (PD), proportional-integral (PI), or proportional-integral-derivative (PID)) may be used to monitor feedstock properties such as flow rates and velocities at a first set-point value (e.g., initialization value). Based on the monitored values, a second set-point value may be converged upon. Using the second set-point value an adjustment value, calibration parameter, a dimensional parameter, an operational parameter, or combination thereof may be determined. For instance, if the spray fixture has a nozzle with an opening that has multiple needle-like pathways, an initial volume emitted may be determined by solving for a total number of pathways that are not closed off by a plate. This initial volume, $V_1$, in some embodiments, may be an initial set-point. Based on monitoring the volumetric flow rate, or based on calculated or desired set-points for a desired flow rate, the initial volume may be increased by moving the plate (e.g., adjusting plate position) associated with blocking the other needle-like pathways, such that a second volume V2 may be converged upon based on the monitored and calculated values of flow rates. It is noted that statistical analysis, regression models, and optimization models (e.g., Monte Carlo method) may be used to converge on the adjustment value, calibration parameter, a dimensional parameter, an operational parameter, or combination thereof.

Referring now to FIG. 14, a system 1400 for spray, emission, extrusion, or delivery, or distribution for nanotechnology applications based on lability characteristics is depicted. In embodiments, the system 1400 includes an applicator 1402 having an adjustable speed. For example, the applicator 1402 may include a tractor, a planter, a conveyor belt, a spray dryer, a continuous coating machine, a rotating drum, a spray fixture, or combinations thereof.

In embodiments, the applicator 1402 has a first port 1404 and a second port 1406, where each of the first port 1404 and the second port 1406 are configured to interchangeably receive one or more components based on lability characteristics of a feedstock. For example, if lability characteristics indicate that the fluid is a highly viscous fluid, then a first one or more components may be interchanged or exchanged with a second one or more components capable of delivering and distributing the highly viscous fluid in a cost-effective manner (e.g., at a low pressure).

In embodiments, the system 1400 is configured to utilize one hopper 1408 of multiple possible feedstock hoppers based on the lability characteristics of the feedstock. For example, a first selected feedstock hopper 1408 may have an open configuration with baffles in order to aid in quick mixing of a feedstock with multiple ingredients (e.g., chitosan, microbes, biologicals, surfactants, emulsifiers, and/or combinations thereof), while a second selected feedstock hopper may be a closed hopper with separate tanks for immiscible or highly labile ingredients. Thus, each of the multiple feed hoppers may have a port (e.g., third port) that is threaded to interface with a port of the applicator (e.g., first port). It is noted that while threading is used as the interfacing mechanisms, other interfacing mechanisms will be recognized by those skilled in the art, and are intended to be encompassed herein. For example, a second interfacing mechanism may include, but is not limited to, a quick release mechanism, a compressible ball-joint assembly, a Swagelok fitting, a gasket assembly, and combinations thereof.

In embodiments, the system 1400 is configured to utilize one or more distribution mechanisms 1410 of multiple possible distribution mechanisms. For example, a selected distribution mechanism 1410 may have a port (e.g., fourth port) configured to interface with a port (e.g., second port) of the applicator. For instance, the distribution mechanism may use threading or another interfacing mechanism to interchangeably interface with a port of the applicator.

In embodiments, the system 1400 is configured to utilize one or more fixtures 1412 of multiple possible fixtures. For example, a selected fixture 1412 may be one of a charged collector fixture, an atomizing fixture, a spray fixture having needle-like columns, a spray fixture having an annular shape or resembling an annulus, a spray fixture with a 360 degree spraying radius, and combinations thereof. It is noted that examples of these and other spray fixtures are described generally in U.S. Pat. No. 9,148,994, issued on Oct. 6, 2015, filed Nov. 12, 2012, by John Alvin Eastin, et al., titled SYSTEMS FOR THE CONTROL AND USE OF FLUIDS AND PARTICLES, which is incorporated herein by reference in its entirety.

In embodiments, the distribution mechanism 1410 is coupled with the feedstock hopper 1408 via one or more delivery mechanisms 1414 and configured to spray or emit the feedstock at least proportionally to the adjustable speed of the applicator and according to the lability characteristics of the feedstock. For example, if the applicator utilizes a conveyor belt, the conveyor belt may have a mechanical, electrical, or communicative connection with the applicator and/or delivery mechanism such that the speed of extrusion, emission, delivery, or distribution from the selected distribution mechanism 1410 is proportional to the speed of the conveyor belt.

In embodiments, the system 1400 includes a processor and a memory. For example, the applicator 1402 may be a component of a controllable area network (CAN) having a bus, a memory, a processor. In some embodiments, the memory and the processor are configured with logical instructions (e.g., embedded or programmed into the memory) to perform the acts or steps of the methods disclosed herein.

In embodiments, the system 1400 has a display 1416 for displaying results of the methods disclosed herein. For example, the applicator 1402 may include a lab-top equipment with a display 1416 and a user interface. The display 1416 may display one or more queries, a checklist, and/or instructions for determining which applicator, spray fixture, and/or application configuration should be used for a nanotechnology application. For instance, the display 1416 may display 1) the selected feedstock hopper 1408 and the selected distribution mechanism 1410 based on the limited spectrum of selection criteria or configuration criteria and/or processes for making the respective selections, and 2) at least one of: the adjustment, the calibration, the dimensional, and the operational parameter. In some embodiments, displaying the selected distribution mechanism 1410 include displaying a selected spray fixture 1412 of multiple possible spray fixtures.

In embodiments, the display 1416 is configured to display operational and assembly instructions. In some embodiments, the display may be attached to a spray vehicle for displaying spray or emission parameters to an operator of the vehicle.

In embodiments, the display 1416 is communicatively coupled with a server 1418 or other memory storage device. The server 1418 may include or be communicatively coupled with multiple databases. In some embodiments, the multiple databases may be separately configured for intended nanotechnology applications. In other embodiments, the multiple databases may be separately configured for intended nanotechnology applications and selection criteria and configuration criteria for fixtures and applicators for the intended nanotechnology application.

In embodiments, the display 1416 may be a component of a mobile device 1420 (e.g., smart phone, tablet, laptop computer, etc.) with a transceiver configured for communicating with the server 1418. In this regard, the selection of a hopper 1408, a selection of a distribution mechanism 1410, a selection of a fixture 1412, and/or a selection of an applicator 1402 or an applicator configuration may be performed from the mobile device 1420.

In embodiments, the nanotechnology application is performed according the various determinations made. Performing the application may include delivering feedstock to a distribution mechanism such as a nozzle. In embodiments, the delivery of feedstock to the distribution mechanism is at a low pressure (e.g., 1-15 psi). For example, delivery may include using a low pressure delivery mechanism such as a fluid drilling machine that uses one or more fluid drilling augers may be used to deliver feedstock to a nozzle. By way of another example, delivery may include using a low pressure peristaltic pump. However, the use of the peristaltic pump is not limiting, as delivery may take place using any positive displacement pump. In this regard, it is noted that many positive displacement pumps result excessive cavitation, detrimentally affecting the integrity of the pump or other components of a distribution or delivery mechanism. Therefore, in some embodiments, a pulse dampener is used to aid in delivery of the feedstock to a distribution mechanism.

In embodiments, the distribution mechanism may vary or is adjustable based on the dedicated process for which it is being used.

It is noted that for purposes of determining flow rates, or a mechanical energy balance, in some embodiments a working form of Bernoulli's equation (BE) may be used as follow:

$$\Delta\left(\frac{P}{\rho} + gz + \frac{V^2}{2}\right) = \frac{DW_{n.f.}}{dm} - \tilde{F}$$

In other embodiments, a head form of BE may be used as follows:

$$\Delta\left(\frac{P}{\rho g} + z + \frac{V^2}{2g}\right) = \frac{DW_{n.f.}}{g\,dm} - \tilde{F}/g$$

It is noted that when a mass balance is performed for a sudden expansion, the following relationship may be applicable:

$$V_2 = \frac{V_2^2 - V_1^2}{2}$$

Referring now to FIG. 15, a sectional view of an embodiment of a pulse dampener 1500 is depicted. Pulse dampener 1500 may include one or more cavities 1502 and one or more channels 1504. In some embodiments, the pulse dampener 1500 includes multiple cavities 1502 successively coupled using multiple channels 1504. In this regard, flow from the positive displacement pump may enter a first channel 1504 and exit a last channel 1504, where one or more channels 1504 may be between the first and the last channel 1504. It is further noted that although channels 1504 are depicted as having parallel sides, this depiction is not limiting. For example, in some embodiments, the channels 1504 may have contracting sides or expanding sides (e.g., sides configured to contract or expand fluid flowing through them).

In some embodiments, the methods disclosed herein may include using a formula, model, or relationship to predict flow characteristics. For example, Bernoulli's Equation may be used to understand and predict flow characteristics into, through, and out of the pulse dampener 1500, according to the following:

$$\Delta\left(\frac{P}{\rho} + gz + \frac{V^2}{2}\right) = \frac{dW_{n.f.}}{dm} - F$$

where F is the friction heating term per unit mass. In embodiments, the friction heating term may be proportional to diameter of the channel 1504 (D1) and diameter (e.g., or height) of chamber 1502 (D2) according to the following:

$$F = K\frac{V^2}{2}$$

where K is the resistance coefficient, V is the largest of the two velocities. In embodiments incorporating a sudden expansion or enlargement K may be related to the two pipe diameters (e.g., entrance pipe and chamber pipe, or height of chamber) according to the following:

$$K = \left[1 - \frac{D_1^2}{D_2^2}\right]^2$$

For example, flow entering channel 1504 from a positive displacement pump may flow into a first cavity 1502 where it encounters a large mass of fluid within the cavity 1502. This encounter of flow with a large mass results a number of random/chaotic eddies. Not only do these eddies help to transfer kinetic-pulsating energy resulting from the pump, but they also help enable further mixing, which may contribute to emulsion formation. Using Bernoulli's Equation and a point near the fluid entrance and a point far from the fluid entrance, where velocity is negligible, a relationship of fluid flow characteristics is determined according to the following:

$$P_2 - P_1 = \frac{\rho V_1^2}{2} - \rho F$$

The above equation assumes that the potential energy term is negligible. As this is not always the case in pulse dampener 1500, other forms of Bernoulli's equation may be derived. Further, as the channels may gradually contract or expand, instead of using sudden contraction and/or expansion, the forms Bernoulli's equation may take may again vary.

It is to be understood that embodiments of the methods according to the inventive concepts disclosed herein may include one or more of the steps described herein. Further, such steps may be carried out in any desired order and two or more of the steps may be carried out simultaneously with one another. Two or more of the steps disclosed herein may be combined in a single step, and in some embodiments, one or more of the steps may be carried out as two or more sub-steps. Further, other steps or sub-steps may be carried in addition to, or as substitutes to one or more of the steps disclosed herein.

From the above description, it is clear that the inventive concepts disclosed herein are well adapted to carry out the objects and to attain the advantages mentioned herein as well as those inherent in the inventive concepts disclosed herein. While presently preferred embodiments of the inventive concepts disclosed herein have been described for purposes of this disclosure, it will be understood that numerous changes may be made which will readily suggest themselves to those skilled in the art and which are accomplished within the broad scope and coverage of the inventive concepts disclosed and claimed herein.

What is claimed:

1. A method for labile-based delivery and distribution for nanotechnology applications, comprising:

determining a lability reference frame for a feedstock, the lability reference frame including one of a pH reference frame, a pressure reference frame, a temperature reference frame, a chemical reactivity reference frame, or an emulsion reference frame;

comparing first lability characteristics of the feedstock at a first point in the lability reference frame with second lability characteristics of the feedstock at a second point in the lability reference frame to determine a level of lability;

limiting a spectrum of selection criteria or configuration criteria based on the level of lability, the limiting a spectrum of selection criteria or configuration criteria based on the level of lability comprising limiting a selection criteria for selecting at least one of a fixture, an applicator, or an applicator configuration for a nanotechnology application; and applying the feedstock via a selection of the at least one of the fixture, an applicator, or an applicator configuration for a nanotechnology application;

monitoring, via a feedback controller, one or more feedstock properties different from the first lability characteristics and the second lability characteristics to determine a first set-point value of the one or more feedstock properties; and adjusting the one or more feedstock properties to a second set-point value based on an output of the feedback controller, wherein the one or more feedstock properties include one of a velocity of a sprayed feedstock or a flow rate of the sprayed feedstock.

2. The method of claim 1, wherein the nanotechnology application comprises at least one of: a nanomedicine application, a nano-suspension application including colloids, a nanopillar application, a tissue engineering application, a drug delivery application, a semiconductor fabrication application, a nanotube fabrication application, a nanowire fabrication application, and a nano-fuel application.

3. The method of claim 1, wherein adjusting the feedstock property comprises adjusting a plate position of a fixture.

4. The method of claim 3, wherein a number of open needle-like pathways is proportional to the plate position.

5. The method of claim 1, wherein the feedback controller comprises a proportional-derivative controller.

6. The method of claim 1, wherein the feedback controller comprises a proportional-integral controller.

7. The method of claim 1, wherein the feedback controller comprises a proportional-integral-derivative controller.

8. The method of claim 1, wherein the feedback controller comprises a regression model.

9. The method of claim 1, wherein the feedback controller comprises an optimization model.

10. The method of claim 9, wherein the feedback controller further comprises a Monte Carlo method.

* * * * *